US010874733B2

(12) United States Patent
Cho et al.

(10) Patent No.: US 10,874,733 B2
(45) Date of Patent: Dec. 29, 2020

(54) COMPOSITION FOR ENHANCING IMMUNITY COMPRISING IMMUNE MODULATOR AND CATIONIC LIPOSOME, AND USE OF SAME

(71) Applicant: EYEGENE INC., Seoul (KR)

(72) Inventors: Yang Je Cho, Seoul (KR); Kwangsung Kim, Gyeonggi-do (KR); Na Gyong Lee, Seoul (KR); Shin Ae Park, Seoul (KR)

(73) Assignee: EYEGENE INC., Seoul (KR)

( * ) Notice: Subject to any disclaimer, the term of this patent is extended or adjusted under 35 U.S.C. 154(b) by 0 days.

(21) Appl. No.: 16/346,401

(22) PCT Filed: Oct. 30, 2017

(86) PCT No.: PCT/KR2017/012051
§ 371 (c)(1),
(2) Date: Apr. 30, 2019

(87) PCT Pub. No.: WO2018/080253
PCT Pub. Date: May 3, 2018

(65) Prior Publication Data
US 2019/0255171 A1 Aug. 22, 2019

(30) Foreign Application Priority Data

Oct. 31, 2016 (KR) .................. 10-2016-0142703
Aug. 24, 2017 (KR) .................. 10-2017-0107420
Aug. 24, 2017 (KR) .................. 10-2017-0107421

(51) Int. Cl.
*A61K 31/739* (2006.01)
*C08B 37/00* (2006.01)
*C08L 5/00* (2006.01)
*A61K 39/25* (2006.01)
*A61K 9/127* (2006.01)
*A61K 9/19* (2006.01)
*A61K 39/00* (2006.01)
*A61K 39/39* (2006.01)
*A61K 39/002* (2006.01)
*A61K 39/295* (2006.01)
*A61K 39/12* (2006.01)
*A61K 39/108* (2006.01)

(52) U.S. Cl.
CPC ............ *A61K 39/25* (2013.01); *A61K 9/1272* (2013.01); *A61K 9/19* (2013.01); *A61K 31/739* (2013.01); *A61K 39/00* (2013.01); *A61K 39/002* (2013.01); *A61K 39/0258* (2013.01); *A61K 39/12* (2013.01); *A61K 39/295* (2013.01); *A61K 39/39* (2013.01); *C08B 37/006* (2013.01); *C08L 5/00* (2013.01); *Y02A 50/30* (2018.01)

(58) Field of Classification Search
None
See application file for complete search history.

(56) References Cited

U.S. PATENT DOCUMENTS 7,507,802 B2  3/2009  Ahn et al.
2008/0292686 A1* 11/2008  Garcon ............... A61K 9/0021
424/450

FOREIGN PATENT DOCUMENTS

| EP | 2444103 A1 | 4/2012 |
|---|---|---|
| JP | 2012530488 A | 12/2012 |
| KR | 20030090897 A | 12/2003 |
| KR | 20060117387 A | 11/2006 |
| KR | 20120013260 A | 2/2012 |
| KR | 101509456 B1 | 4/2015 |
| WO | WO0156548 A2 | 8/2001 |
| WO | WO2004039413 A1 | 5/2004 |
| WO | WO2005039634 A1 | 5/2005 |
| WO | WO2006121232 A1 | 11/2006 |
| WO | WO2010130897 A1 | 11/2010 |

OTHER PUBLICATIONS

Cross et al., "Phase I study of detoxified *Escherichia coli* J5 lipopolysaccharide (J5dLPS)/group B meningococcal outer membrane protein (OMP) complex vaccine in human subjects" Vaccine vol. 21 pp. 4576-4587 (Year: 2003).*
Guy et al., "Design, characterization and preclinical efficacy of a cationic lipid adjuvant for influenza split vaccine" Vaccine vol. 19 pp. 1794-1805 (Year: 2001).*
Anwekar et al., "Liposomes as drug carriers" International Journal of Pharmacy and Life Sciences vol. 2 No. 7 pp. 945-951 (Year: 2011).*
Whitfield et al., "Assembly of the R1-type core oligosaccharide of *Escherichia coli* lipopolysaccharide" Journal of Endotoxin Research vol. 5 No. 3 pp. 151-156 (Year: 1999).*
Heinrichs et al., "The Assembly System for the outer core portion of R1- and R4-type lipopolysaccharides of *Escherichia coli*" The Journal of Biological CHemistry vol. 273 No. 45 pp. 29497-29505 (Year: 1998).*

(Continued)

*Primary Examiner* — Eric Olson
(74) *Attorney, Agent, or Firm* — Hultquist, PLLC; Steven J. Hultquist

(57) ABSTRACT

The present invention relates to an immunity enhancing composition including an immune response modulator having a novel structure and, more specifically, to an immunity enhancing composition and a use of the same, wherein the immunity enhancing composition includes a lipopolysaccharide (LPS) analogue with reduced toxicity, and a cationic liposome. The present invention overcomes the physicochemical instability of a liposome, is advantageous in terms of production, transportation, and storage, and improves stability, thus being beneficial as an immune delivery system. In addition, the present invention includes an immune response modulator, and a cationic liposome, and thus exhibits an enhanced immunity-improving effect compared to the case in which an immune response modulator is used alone.

14 Claims, 16 Drawing Sheets
(7 of 16 Drawing Sheet(s) Filed in Color)

(56) References Cited

OTHER PUBLICATIONS

Paton et al., "Recombinant Probiotics for Treatment and Prevention of Enterotoxigenic *Escherichia coli* Diarrhea" Gastroenterology vol. 128 pp. 1219-1228 (Year: 2005).*

Erridge et al., "The biological activity of a liposomal complete core lipopolysaccharide vaccine" Journal of Endotoxin Research vol. 8 No. 1 pp. 39-46 (Year: 2002).*

Akira, S., et al., "Pathogen Recognition and Innate Immunity", "Cell", Feb. 24, 2006, pp. 783-801, vol. 124.

Katz, S., et al., "Deacylation of Lipopolysaccharide in Whole *Escherichia coli* During Destruction by Cellular and Extracellular Components of a Rabbit Peritoneal Inflammatory Exudate", "The Journal of Biological Chemistry", 1999, pp. 36579-36584, vol. 274, No. 51.

Raetz, C., et al., "Lipopolysaccharide Endotoxins", "Annu Rev Biochem", 2002, pp. 635-700, vol. 71.

Schnare, M., et al., "Toll-Like Receptors Control Activation of Adaptive Immune Responses", "Nature Immunology", Oct. 2001, pp. 947-950, vol. 2, No. 10.

Schwendener, R., et al., "Liposomes as Vaccine Delivery Systems: A Review of the Recent Advances", "Therapeutic Advances in Vaccines", 2014, pp. 159-182, vol. 2, No. 6.

Han, J. E., et al., "Characterization of the Structure and Immunostimulatory Activity of a Vaccine Adjuvant, De-O-Acylated Lipooligosaccharide", "PLOS ONE", Jan. 2014, pp. e85838: 1-13, vol. 9, No. 1.

Ko, A., et al., "Cellular Immune Response and Protective Immunity to M. Tuberculosis Antigen With a de-O-acylated Lipooligosaccharide-based Adjuvant Systems in Mice", "The 2014 Fall Conference of the Korean Association of Immunologists", Nov. 2014, pp. Poster No. P-197.

Mahapatra, A.K., et al., "Progress With Liposomal Drug Delivery Systems: Formulation to Therapy", "Der Pharmacia Lettre", 2014, pp. 110-128, vol. 6, No. 3.

Arenas, J., "The Role of Bacterial Lipopolysaccharides as Immune Modulator in Vaccine and Drug Development", "Endocrine, Metabolic & Immune Disorders—Drug Targets", Jan. 1, 2012, pp. 221-235, vol. 12.

Somiya, M., et al., "Potential of a Non-Cationic Liposomes-Based Delivery System for Nucleic Acid Medicines", "Drug Delivery System", 2016, pp. 35-43, vol. 31, No. 1.

\* cited by examiner

COMPOSITION FOR ENHANCING IMMUNITY COMPRISING IMMUNE MODULATOR AND CATIONIC LIPOSOME, AND USE OF SAME

CROSS-REFERENCE TO RELATED APPLICATIONS

This application is a U.S. national phase under the provisions of 35 U.S.C. § 371 of International Patent Application No. PCT/KR17/12051 filed Oct. 30, 2017, which in turn claims priority of Korean Patent Application No. 10-2016-0142703 filed Oct. 31, 2016, Korean Patent Application No. 10-2017-0107420 filed Aug. 24, 2017, and Korean Patent Application No. 10-2017-0107421 filed Aug. 24, 2017. The disclosures of such international patent application and Korean priority patent applications are hereby incorporated herein by reference in their respective entireties, for all purposes.

TECHNICAL FIELD

The present invention relates to a composition for enhancing immunity comprising an immune modulator having a novel structure. More particularly, the present invention relates to a composition for enhancing immunity comprising an analogue of lipopolysaccharide (LPS) having reduced toxicity and a cationic liposome, and uses thereof.

BACKGROUND ART

Liposomes have advantages of exhibiting excellent biocompatibility, being easy to manufacture, and being capable of delivering water-soluble and lipid-soluble drugs, and thus research has been actively conducted on such liposomes as a drug delivery system having fewer side effects in vivo. Conventional liposomes have disadvantages of causing aggregation, fusion, hydrolysis of phospholipids, oxidation, leakage of encapsulated drugs and the like, when the liposomes are stored as dispersion phase in an aqueous solution because the system itself is physically and chemically unstable. Therefore, there is a disadvantage in that the stability of the liposome itself needs to be ensured when the liposome is stored for a long period of time. In order to overcome these disadvantages, studies have been actively conducted to improve the stability of liposomes by storing the liposomes in the form of a fine powder in an attempt to overcome the physicochemical instability of the liposomes. However, a freeze-drying process is used in order to convert the liposomes into a fine powder. During such a process, when liposomes are used alone, the stability and homogeneity of the liposomes are deteriorated, and the physical and chemical properties thereof are thus changed. As a result, disadvantageously, the function of the liposomes as a drug delivery system and the immune activity thereof are deteriorated, and toxicity occurs. Therefore, studies are being conducted on a composition that is advantageous for production, storage, and delivery, while maximizing the advantages of liposomes through the addition of a cryoprotectant or the like in order to prevent deformation of liposomes during the freeze-drying process.

Lipopolysaccharide (LPS) is a major component of the outer membrane of gram-negative bacteria and promotes activation of various immune cells, particularly the innate immune responses. LPS activates antigen-presenting cells through the secretion of cytokines by innate immune cells, the expression of costimulatory molecules on antigen-presenting cells and the induction of antigen presentation, and it links innate immune response to adaptive immune response (Akira S, Uematsu S, Takeuchi O, Cell 124: 783-801(2006); Schnare M, Barton G M, Holt A C, Takeda K, Akira S, et al. Nat Immunol 2: 947-950(2001)).

LPS consists of three domains, i.e., an amphiphilic domain (lipid A), a core oligosaccharide (OS), and an O-antigen (or O-antigenic polysaccharide). Lipid A is known to play a role in the endotoxin activity of LPS and to exhibit immunostimulatory effects through TLR4 (toll-like receptor 4) signaling of various types of immune cells (Raetz C R, Whitfield C, Annu Rev Biochem 71: 635-700 (2002)). Lipid A derivatives, which exhibit reduced toxicity, have been targeted for the development of human vaccine immune adjuvants. Monophosphoryl lipid A (MPL) is a non-toxic derivative of LPS isolated from the *Salmonella minnesota* rough strain. In addition, a combination of an aluminum salt with MPL has been approved as an immune adjuvant for vaccines against HBV (hepatitis B virus) and HPV (human papillomavirus).

LPS has been known to have an anticancer effect since the 1950s, but has been unsuitable for use due to toxicity capable of causing death from sepsis even with contamination at the nanogram (ng) level. Thus, studies have been steadily made to reduce the toxicity of LPS and the toxicity of LPS has been successfully reduced, particularly through removal of polysaccharide chains or deacylation of lipid A (Katz S S et al., J Biol Chem. December 17; 274(50:36579-84, 1999). In particular, the MPL obtained through phosphorylation of lipid A, obtained by removing the polysaccharide chain of LPS, has been developed as an immune anticancer agent free of LPS toxicity, but the effects thereof are known to be insufficient.

As a result of efforts to develop an LPS analogue capable of exhibiting excellent immunostimulatory activity while reducing toxicity which has been a problem caused by a use of conventional LPS, and to overcome the physical and chemical instability of liposomes, the present inventors found an EG-immune modulator (EG-IM) having a novel structure and reduced toxicity by isolating and purifying LOS not having an O-antigen site from an *E. coli* strain found in a human intestine, and deacylating the same, and identified that a vaccine composition containing the immune modulator and a cationic liposome exhibits excellent immunostimulatory activity. Based on the finding, the present invention has been completed.

DISCLOSURE

Technical Problem

Therefore, it is one object of the present invention to provide a composition for enhancing immunity comprising: (a) an immune modulator represented by the following Formula 1; and (b) a cationic liposome:

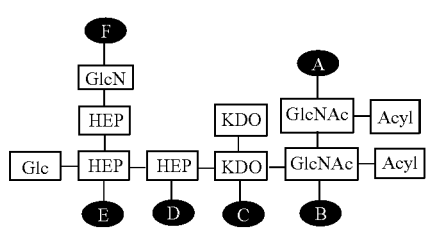

[Formula 1]

wherein Glc is glucose, GlcN is glucosamine, HEP is heptose, KDO is 2-keto-3-deoxy-octonate, GlcNAc is N-acetylglucosamine, and A to F are positions to which phosphate can be bonded.

It is another object of the present invention to provide a vaccine composition comprising (a) an antigen and (b) the composition for enhancing immunity as an active ingredient.

It is another object of the present invention to provide a method for preparing a composition for enhancing immunity comprising: (a) preparing a solution containing an immune modulator represented by Formula 1; (b) dissolving a lipid in an organic solvent to prepare a lipid mixed solution; (c) lyophilizing the lipid mixed solution of step (b) to remove the organic solvent; and (d) rehydrating the substance obtained in step (c) and then mixing the substance with the solution of step (a), thereby forming a composition for enhancing immunity.

It is another object of the present invention to provide a method for preparing a vaccine composition comprising: (a) preparing a solution containing an immune modulator represented by Formula 1; (b) dissolving a lipid in an organic solvent to prepare a lipid mixed solution; (c) lyophilizing the lipid mixed solution of step (b) to remove the organic solvent; (d) rehydrating the substance obtained in step (c), thereby forming a liposome; and (e) adding the solution of step (a) and an antigen to the liposome of step (d), followed by lyophilizing again.

Technical Solution

To achieve the above object, the present invention provides a composition for enhancing immunity comprising: (a) an immune modulator represented by the following Formula 1; and (b) a cationic liposome:

[Formula 1]

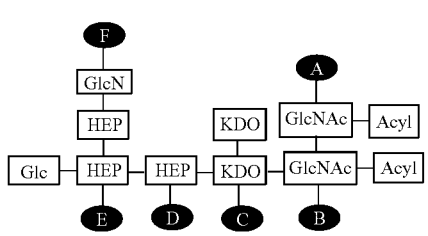

wherein Glc is glucose, GlcN is glucosamine, HEP is heptose, KDO is 2-keto-3-deoxy-octonate, GlcNAc is N-acetylglucosamine, and A to F are positions to which phosphate can be bonded.

The present invention also provides a vaccine composition comprising (a) an antigen; and (b) the composition for enhancing immunity as an active ingredient.

The present invention also provides a method for preparing a composition for enhancing immunity comprising: (a) preparing a solution containing an immune modulator represented by Formula 1; (b) dissolving a lipid in an organic solvent to prepare a lipid mixed solution; (c) lyophilizing the lipid mixed solution of step (b) to remove the organic solvent; and (d) rehydrating the substance obtained in step (c) and then mixing the substance with the solution of step (a), thereby forming a composition for enhancing immunity.

The present invention also provides a method for preparing a vaccine composition comprising: (a) preparing a solution containing an immune modulator represented by Formula 1; (b) dissolving a lipid in an organic solvent to prepare a lipid mixed solution; (c) lyophilizing the lipid mixed solution of step (b) to remove the organic solvent; (d) rehydrating the substance obtained in step (c), thereby forming a liposome; and (e) adding the solution of step (a) and an antigen to the liposome of step (d), followed by lyophilizing again.

The present invention also provides a method for preventing an immune disease including treating a patient with the immune modulator represented by Formula 1 and a use of the immune modulator for the prevention of an immune disease.

The patent or application file contains at least one drawing executed in color. Copies of this patent or patent application publication with color drawing(s) will be provided by the Office upon request and payment of the necessary fee.

BRIEF DESCRIPTION OF THE DRAWINGS

FIGS. 19 to 21 show the results of analysis of the synergistic effects upon addition of a lipid ingredient to a varicella-zoster virus vaccine containing liposomal EG-IM, wherein FIG. 19 shows the result upon addition of cholesterol, FIG. 20 shows the result upon addition of squalene, and FIG. 21 shows the result upon addition of tricaprin.

Figure 1:
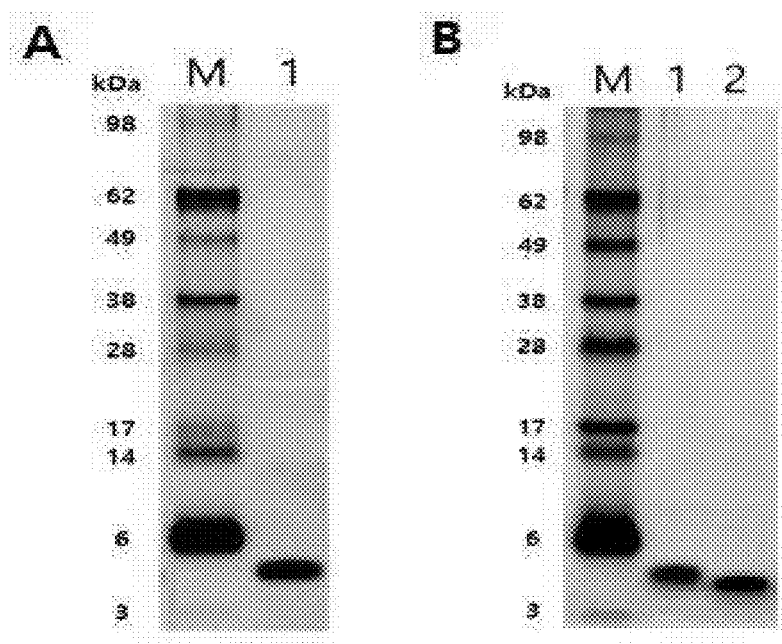
FIG. 1 in image A shows the results of identification of the extracted LOS through electrophoresis and silver staining, and in image B shows a result indicating that the size of EG-IM decreases, based on LOS extracted by O-acyl chain removed lipid A when treating LOS with an alkali, wherein M represents a marker, lane 1 represents LOS extracted before deacylation, and lane 2 represents an immune modulator (EG-IM).

DETAILED DESCRIPTION OF THE INVENTION

Unless defined otherwise, all technical and scientific terms used herein have the same meanings as appreciated by those skilled in the field to which the present invention pertains. In general, the nomenclature used herein and the experimentation method described below are well-known in the art and are ordinarily used.

In one embodiment of the present invention, a liposomal EG-IM was prepared by mixing a lipid mixed solution containing a mixture of DMPC and DOTAP with an EG-immune modulator (EG-IM) solution to prepare a lipid mixed solution containing EG-IM followed by rehydration, and the effects of the liposomal EG-IM on the proliferation of immune cells and reduction of cytotoxicity were identified using a mouse macrophage cell line.

Accordingly, in one aspect, the present invention is directed to a composition for enhancing immunity comprising: (a) an EG-immune modulator (EG-IM) represented by the following Formula 1; and (b) a cationic liposome:

[Formula 1]

wherein Glc is glucose, GlcN is glucosamine, HEP is heptose, KDO is 2-keto-3-deoxy-octonate, GlcNAc is N-acetylglucosamine, and A to F are positions to which phosphate can be bonded.

In another aspect, the present invention is directed to a method for preparing the composition for enhancing immunity, and the composition for enhancing immunity may be prepared through the following steps:

(a) preparing a solution containing an immune modulator represented by Formula 1:

[Formula 1]

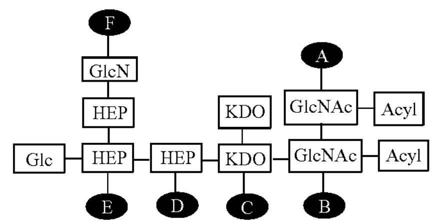

wherein Glc is glucose, GlcN is glucosamine, HEP is heptose, KDO is 2-keto-3-deoxy-octonate, GlcNAc is N-acetylglucosamine, and A to F are positions to which phosphate can be bonded;

(b) dissolving a lipid in an organic solvent to prepare a lipid mixed solution;

(c) lyophilizing the lipid mixed solution of step (b) to remove the organic solvent; and (d) rehydrating the substance obtained in step (c) and then mixing the substance with the solution of step (a), thereby forming a composition for enhancing immunity.

The EG-immune modulator (EG-IM) according to the present invention may be represented by the following Formula 1:

[Formula 1]

wherein Glc is glucose, GlcN is glucosamine, HEP is heptose, KDO is 2-keto-3-deoxy-octonate, GlcNAc is N-acetylglucosamine, and A to F are positions to which phosphate can be bonded.

As used herein, the term "LOS (lipooligosaccharide)" refers to a variant of LPS (lipopolysaccharide) that has a shorter sugar chain than natural LPS and thus has a lower molecular weight. LOS prior to deacylation preferably has a molecular weight of 3,000 to 10,000 Da, more preferably 3,000 to 4,000 Da. The term "deacylated LOS" refers to LOS in which the fatty acid linked to the glucosamine of lipid A via a —C(O)O— bond is removed therefrom and the toxicity is greatly reduced compared to LOS. The fatty acid is linked to lipid A glucosamine via —C(O)O— and —C(O)NH— bonds. The deacylated LOS of the present invention is LOS from which the fatty acid linked via the —C(O)O— bond is removed through deacylation of lipid A.

The EG-IM can be prepared by various methods, but can be prepared in accordance with the methods disclosed in the preceding patents of the present inventors, namely Korean Patent No. 0456681; WO 2004/039413; Korean Patent No. 0740237; and WO 2006/121232. For example, LPS is deacylated by treatment with a strong base (e.g., 0.2 N NaOH) to remove some fatty acids from lipid A to thereby detoxify the same.

According to the present invention, the EG-IM can be linked to 2 to 6 phosphate groups, preferably 3 to 4 phosphate groups, but is not limited thereto. In addition, the number and positions of the phosphate groups in Formula 1 may be the same as those exemplified in Table 1 below.

TABLE 1

| Item | Number of phosphate groups | Positions of phosphate groups |
| --- | --- | --- |
| Example 1 | 2 | A, B |
| Example 2 | 2 | A, C |
| Example 3 | 2 | A, D |
| Example 4 | 2 | A, E |
| Example 5 | 2 | A, F |
| Example 6 | 2 | B, C |
| Example 7 | 2 | B, D |
| Example 8 | 2 | B, E |
| Example 9 | 2 | B, F |
| Example 10 | 2 | C, D |
| Example 11 | 2 | C, E |
| Example 12 | 2 | C, F |
| Example 13 | 2 | D, E |
| Example 14 | 2 | D, F |
| Example 15 | 2 | E, F |
| Example 16 | 3 | A, B, C |
| Example 17 | 3 | A, B, D |
| Example 18 | 3 | A, B, E |
| Example 19 | 3 | A, B, F |
| Example 20 | 3 | A, C, D |
| Example 21 | 3 | A, C, E |
| Example 22 | 3 | A, C, F |
| Example 23 | 3 | A, D, E |
| Example 24 | 3 | A, D, F |
| Example 25 | 3 | A, E, F |
| Example 26 | 3 | B, C, D |
| Example 27 | 3 | B, C, E |
| Example 28 | 3 | B, C, F |
| Example 29 | 3 | B, D, E |
| Example 30 | 4 | B, D, F |
| Example 31 | 3 | B, E, F |
| Example 32 | 3 | C, D, E |
| Example 33 | 3 | C, D, F |
| Example 34 | 3 | C, E, F |
| Example 35 | 3 | D, E, F |
| Example 36 | 4 | A, B, C, D |
| Example 37 | 4 | A, B, C, E |
| Example 38 | 4 | A, B, C, F |
| Example 39 | 4 | A, B, D, E |
| Example 40 | 4 | A, B, D, F |
| Example 41 | 4 | A, B, E, F |
| Example 42 | 4 | A, C, D, E |
| Example 43 | 4 | A, C, D, F |
| Example 44 | 4 | A, D, E, F |
| Example 45 | 5 | A, B, C, D, E |
| Example 46 | 5 | A, B, C, D, F |
| Example 47 | 6 | A, B, C, D, E, F |

The phosphate is bonded at a position selected from the group consisting of AB, AC, AD, AE, AF, BC, BD, BE, BF, CD, CE, CF, DE, DF, EF, ABC, ABD, ABE, ABF, ACD, ACE, ACF, ADE, ADF, AEF, BCD, BCE, BCF, BDE, BDF, BEF, CDE, CDF, CEF, DEF, ABCD, ABCE, ABCF, ABDE, ABDF, ABEF, ACDE, ACDF, ADEF, BCDE, BCDF, BCEF, BDEF, CDEF, ABCDE, ABCEF and ABCDEF of Formula 1.

According to the present invention, the sugar in Formula 1 is selected from the group consisting of hexose, hexosamine, N-acetylhexosamine, heptose and Kdo (2-keto-3-deoxy-octonate).

As used herein, the term "hexose" means a monosaccharide including six carbon atoms in a molecule, and examples thereof include, but are not limited to, ketohexose (psicose, fructose, sorbose, tagatose), aldohexose (allose, altrose, glucose, mannose, gulose, idose, galactose, talose) and deoxy sugars (fucose, fuculose, rhamnose).

According to the present invention, the hexose is aldohexose, and in a specific example, the aldohexose is glucose or galactose.

As used herein, the term "heptose" refers to a monosaccharide containing seven carbon atoms in a molecule, and may be classified into aldoheptose (position 1) and ketoheptose (position 2) according to the position of functional groups (aldehyde and ketone groups). The aldoheptose is, for example, L-glycero-D-manno-heptose, but is not limited thereto. The ketoheptose is, for example, sedoheptulose and mannoheptulose, but is not limited thereto.

According to the present invention, the hexosamine is glucosamine, galactosamine or mannosamine, and in a specific example, the hexosamine is glucosamine.

According to the present invention, the N-acetylhexosamine is N-acetylglucosamine, N-acetylgalactosamine or N-acetylmannosamine, and in a specific example, the N-acetylhexosamine is N-acetylglucosamine.

The EG-IM of the present invention has fewer sugars than wild-type LPS. According to the present invention, the EG-IM may include 5 to 7 sugars. In a specific example, the EG-IM includes 6 or 7 sugars, but is not limited thereto.

The EG-IM of the present invention does not have O-linked fatty acids.

The EG-IM of the present invention is characterized in that it has remarkably reduced toxicity because a fatty acid (for example, a C14 fatty acid) is removed (deacylated) from lipid A. The fatty acid is linked to glucosamine in lipid A via a —C(O)O— or —C(O)NH— bond. In the present invention, deacylation means removal of a fatty acid linked via a —C(O)O— bond.

The deacylation may be carried out by treating LOS with an alkali, and the alkali includes NaOH, KOH, Ba(OH)$_2$, CsOH, Sr(OH)$_2$, Ca(OH)$_2$, LiOH, RbOH, and Mg(OH)$_2$, more preferably Na$_0$H, KOH, Ba(OH)$_2$, Ca(OH)$_2$, LiOH and Mg(OH)$_2$, even more preferably NaOH, KOH and Mg(OH)$_2$, and most preferably NaOH.

According to the present invention, the EG-IM of the present invention is derived from E. coli, and the E. coli is Escherichia coli EG0024 (Accession No.: KCTC 12948BP).

The strain was deposited on Nov. 19, 2015 with the deposit number KCTC 12948BP in the Korean Collection for Type Cultures of the Korea Research Institute of Bioscience and Biotechnology.

The EG-IM of the present invention is particularly suitable for the vaccine composition of the present invention because it exhibits excellent immunostimulatory effects and reduced toxicity, as compared to conventional immune adjuvants. The EG-IM of the present invention is less toxic than MPL (monophosphoryl lipid A), obtained through phosphorylation of lipid A, obtained by removing the polysaccharide chain of LPS in order to remove the toxicity of LPS.

The cationic liposome according to the present invention is a cationic lipid selected from the group consisting of dimethyldioctadecylammonium bromide (DDA), 1,2-dioleoyl-3-trimethylammonium propane (DOTAP), 3β-[N—(N',N'-dimethylaminoethane) carbamoyl] cholesterol (DC-Chol), 1,2-dioleoyloxy-3-dimethylammonium propane (DODAP), 1,2-di-O-octadecenyl-3-trimethylammonium propane (DOTMA), 1,2-dimyristoleoyl-sn-glycero-3-ethylphosphocholine (14:1 Ethyl PC), 1-palmitoyl-2-oleoyl-sn-glycero-3-ethylphosphocholine (16:0-18:1 Ethyl PC), 1,2-dioleoyl-sn-glycero-3-ethylphosphocholine (18:1 Ethyl PC), 1,2-distearoyl-sn-glycero-3-ethylphosphocholin (18:0 Ethyl PC), 1,2-dipalmitoyl-sn-glycero-3-ethylphosphocholine (16:0 Ethyl PC), 1,2-dimyristoyl-sn-glycero-3-ethylphosphocholine (14:0 Ethyl PC), 1,2-dilauroyl-sn-glycero-3-ethylphosphocholin (12:0 Ethyl PC), N1-[2-((1S)-1-[(3-aminopropyl)amino]-4-[di(3-amino-propyl)amino]butylcarboxamido)ethyl]-3,4-di[oleyloxy]-benzamide (MVL5), 1,2-dimyristoyl-3-dimethylammonium-propane (14:0 DAP), 1,2-dipalmitoyl-3-dimethylammonium-propane (16:0 DAP), 1,2-distearoyl-3-dimethylammonium-propane (18:0 DAP), N-(4-carboxybenzyl)-N,N-dimethyl-2,3-bis(oleoyloxy)propan-1-aminium (DOBAQ), 1,2-stearoyl-3-trimethylammonium-propane (18:0 TAP), 1,2-dipalmitoyl-3-trimethylammonium-propane (16:0 TA), 1,2-dimyristoyl-3-trimethylammonium-propane (14:0 TAP) and N4-cholesteryl-spermine (GL67). The cationic liposome may be used alone or in combination with a neutral lipid selected from the group consisting of 1,2-dimyristoyl-sn-glycero-3-phosphorylcholine (DMPC), 1,2-dioleoyl-sn-glycero-3-phosphocholine (DOPC), 1,2-dioleoyl-sn-glycero-3-phosphoethanolamine (DOPE), 1,2-dipalmitoyl-sn-glycero-3-phosphocholine (DPPC), 1,2-distearoyl-sn-glycero-3-phosphocholine (DSPC), 1,2-dilinoleoyl-sn-glycero-3-phosphocholine (DLPC), phosphoethanol amine (PE), and phosphatidyl choline (PC). In one embodiment of the present invention, a combination of DOTAP and DMPC (DOTAP:DMPC), a combination of DDA and DOPC (DDA:DOPC), and a combination of DDA and DMPC (DDA:DMPC) were mainly used.

As used herein, the term "immunostimulation" refers to inducing an initial immune response or increasing a conventional immune response to an antigen to a measurable extent.

In another embodiment of the present invention, a liposomal EG-IM was prepared by mixing a lipid mixed solution containing a mixture of DMPC and DOTAP with an EG-immune modulator (EG-IM) solution to prepare a lipid mixed solution containing EG-IM followed by rehydration, then a vaccine was prepared by adding an antigen to the liposomal EG-IM, and, in order to identify the efficacies of the vaccine, the vaccine prepared by mixing the liposomal EG-IM with each of a recombinant Zika virus envelope protein, a Japanese encephalitis virus (JEV) antigen, recombinant tuberculosis antigens, namely Ag85A, ESAT-6 and HspX, an acellular pertussis vaccine (aP) antigen, and a recombinant varicella-zoster virus (VZV) gE antigen was administered to mice, antibody titers thereof were measured and cytokines were analyzed. As a result, it was found that each of the vaccines has excellent antibody-mediated immune efficacy and/or cellular immune efficacy.

Accordingly, in another aspect, the present invention is directed to a vaccine composition comprising an antigen and the composition for enhancing immunity as an active ingredient.

In another aspect, the present invention is directed to a method for preparing the vaccine composition, and the vaccine composition may be prepared through the following steps:

(a) preparing a solution containing an immune modulator represented by the following Formula 1:

[Formula 1]

wherein Glc is glucose, GlcN is glucosamine, HEP is heptose, KDO is 2-keto-3-deoxy-octonate, GlcNAc is N-acetylglucosamine, and A to F are positions to which phosphate can be bonded;

(b) dissolving a lipid in an organic solvent to prepare a lipid mixed solution;

(c) lyophilizing the lipid mixed solution of step (b) to remove the organic solvent;

(d) rehydrating the substance obtained in step (c), thereby forming a liposome; and (e) adding the solution of step (a) and an antigen to the liposome of step (d), followed by lyophilizing again.

As used herein, the term "antigen" refers to a substance that induces an immune response of an acceptor. Therefore, in the present invention, any substance exhibiting such activity of inducing an immune response can be used without limitation.

The antigen of the present invention may be a peptide, a protein, a nucleic acid, a sugar, a pathogen, an attenuated pathogen, an inactivated pathogen, a virus, a virus-like particle (VLP), a cell or a cell fragment.

In the present invention, the antigen may be an antigen of Zika virus, an antigen of Japanese encephalitis virus, an antigen of *Mycobacterium tuberculosis*, an antigen of pertussis, an antigen of varicella-zoster virus, an antigen of *Haemophilus influenzae* type B (HIB), an antigen of Middle East Respiratory Syndrome (MERS) virus, an antigen of *Pseudomonas aeruginosa*, an antigen of anthrax, an antigen of hepatitis A virus (HAV), an antigen of hepatitis B virus (HBV), an antigen of hepatitis C virus (HCV), an antigen of human immunodeficiency virus (HIV), an antigen of herpes simplex virus (HSV), an antigen of *Neisseria meningitidis*, an antigen of *Corynebacterium diphtheria*, an antigen of *Bordetella pertussis*, an antigen of *Clostridium tetani*, an antigen of human papilloma virus (HPV), an antigen of Enterococci, an antigen of *Staphylococcus aureus*, an antigen of *Klebsiella pneumoniae*, an antigen of *Acinetobacter baumannii*, an antigen of *Enterobacter*, an antigen of *Heli-* cobacter pylori, an antigen of malaria, an antigen of a dengue virus, an antigen of *Orientia tsutsugamushi*, an antigen of severe fever with thrombocytopenia syndrome Bunyavirus (SFTS Bunyavirus), an antigen of severe acute respiratory syndrome-coronavirus (SARS-CoV), an antigen of an influenza virus, an antigen of an Ebola virus and an antigen of *Diplococcus pneumoniae*. In one embodiment of the present invention, the immunogenicity enhancement effect of the present invention was identified through an antigen of Zika virus, an antigen of Japanese encephalitis virus, an antigen of *mycobacterium tuberculosis*, an antigen of pertussis and an antigen of varicella-zoster virus.

The vaccine according to the present invention may be used for preventing or treating a disease, and the vaccine may be in the form of an inactivated vaccine, an attenuated vaccine, a subunit vaccine, a conjugate vaccine, a recombinant vaccine, a monovalent vaccine, a multivalent vaccine, or a mixed vaccine.

In addition, the vaccine according to the present invention can be a Zika vaccine, a Japanese encephalitis vaccine, a tuberculosis vaccine, a pertussis vaccine, a varicella-zoster virus (VZV) vaccine, a varicella vaccine, a *Haemophilus influenzae* type B vaccine, a MERS vaccine, a *Pseudomonas aeruginosa* vaccine, a cancer vaccine, an anthrax vaccine, an HAV vaccine, an HBV vaccine, an HCV vaccine, an HIV vaccine, a meningococcal vaccine, a diphtheria vaccine, a tetanus vaccine, a multidrug-resistant bacteria vaccine, an Enterococci vaccine, a *Staphylococcus aureus* vaccine, a *Klebsiella pneumoniae* vaccine, an *Acinetobacter baumannii* vaccine, an *Enterobacter* vaccine, a *Helicobacter pylori* vaccine, a malaria vaccine, a dengue virus vaccine, an *Orientia tsutsugamushi* vaccine, a severe fever with thrombocytopenia syndrome Bunyavirus (SFTS bunyavirus) vaccine, a severe acute respiratory syndrome-coronavirus (SARS-CoV) vaccine, an Ebola virus vaccine, an influenza virus vaccine, or a *Diplococcus pneumoniae* vaccine.

The cancer vaccine may be selected from the group consisting of vaccines of fibrosarcoma, bladder cancer, pituitary adenoma, glioma, brain tumors, nasopharyngeal cancer, laryngeal cancer, thymoma, mesothelioma, breast cancer, lung cancer, gastric cancer, esophageal cancer, colon cancer, liver cancer, pancreatic cancer, pancreatic endocrine tumor, gallbladder cancer, penile cancer, ureteral cancer, renal cell carcinoma, prostate cancer, non-Hodgkin's lymphoma, myelodysplastic syndrome, multiple myeloma, plasma cell tumor, leukemia, pediatric cancer, skin cancer, ovarian cancer, and cervical cancer, but is not limited thereto.

The vaccine according to the present invention may be a simple mixture formulation or a lyophilized formulation.

The vaccine according to the present invention may contain the antigen descried above, the immune modulator represented by Formula 1 and the cationic liposome in one container (all-in-one vaccine). Based on this feature, the vaccine can be prepared in a ready-to-use form. Preferably, the varicella zoster virus vaccine, i.e., the herpes zoster vaccine or varicella vaccine, can be prepared in a ready-to-use form.

Figure 19:
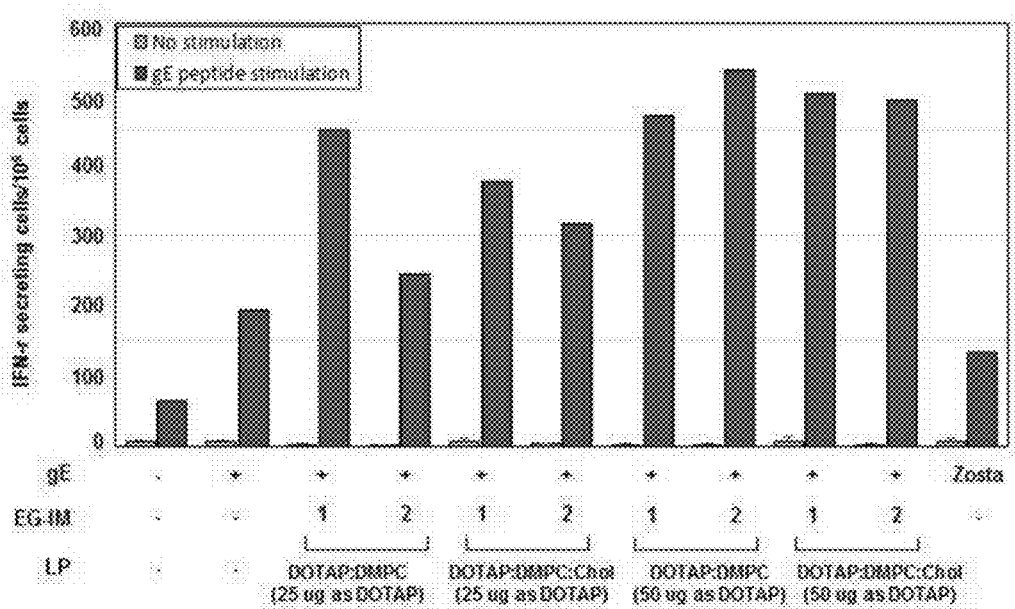
Figure 20:
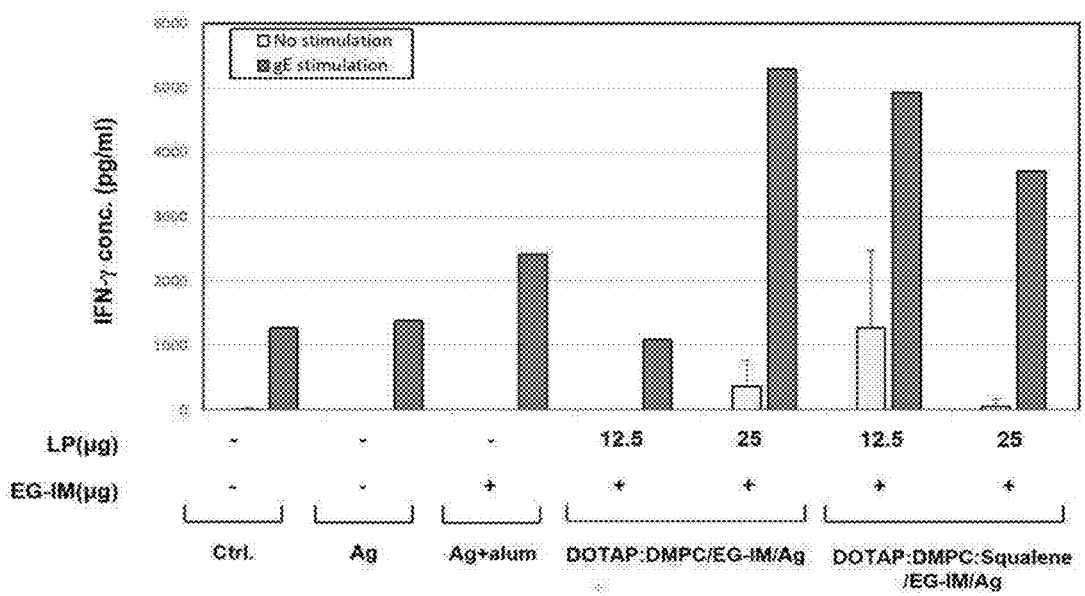
Figure 21:
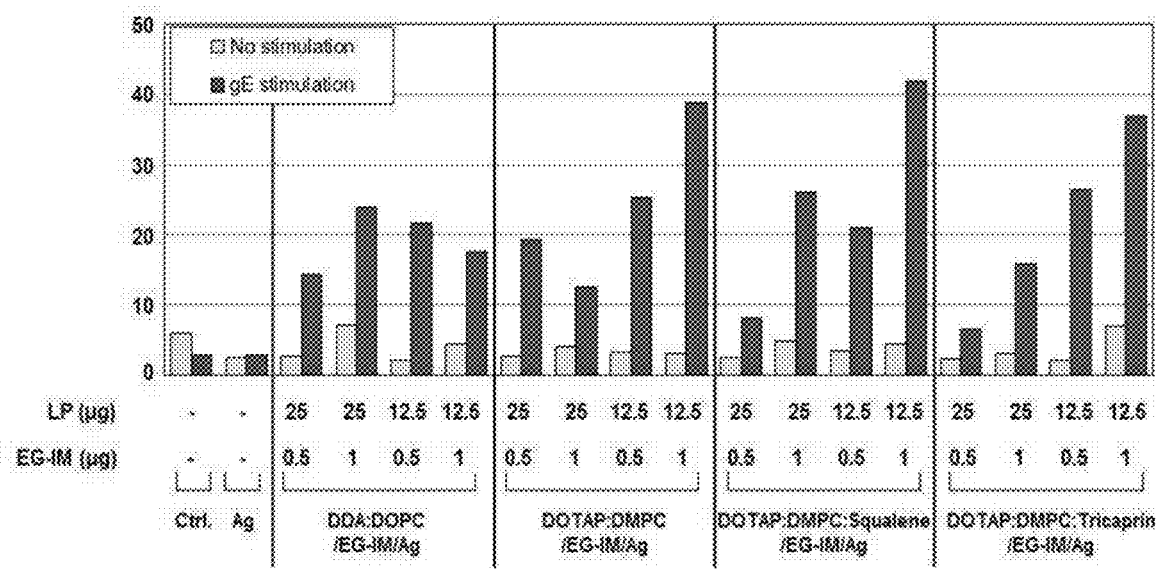

In addition, the vaccine of the present invention may further contain a lipid ingredient acceptable in the art, and in one embodiment of the present invention, a vaccine further containing cholesterol, squalene or tricaprin was prepared, and the immunogenicity enhancement effect thereof was identified (FIGS. 19 to 21).

Figure 22:
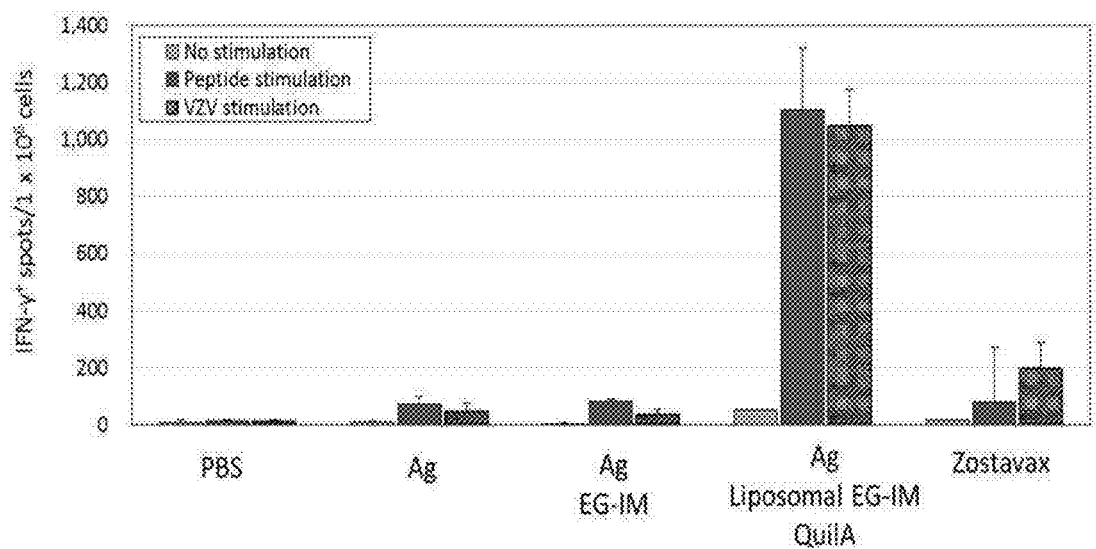
FIG. 22 shows the synergistic effect upon addition of a saponin-based immune adjuvant ingredient to a varicella-zoster virus vaccine containing liposomal EG-IM.

In addition, the vaccine of the present invention may further contain saponin, Quil A, QS21 or the like as an immune adjuvant acceptable in the art. In one embodiment of the present invention, a vaccine containing Quil A, a saponin-derived substance, was prepared, and the immunogenicity enhancement effect thereof was identified (FIG. 22).

The vaccine composition of the present invention may contain a pharmaceutically acceptable carrier, and may contain an ingredient generally used for formulation, such as lactose, dextrose, sucrose, sorbitol, mannitol, starch, acacia gum, calcium phosphate, alginate, gelatin, calcium silicate, microcrystalline cellulose, polyvinyl pyrrolidone, cellulose, water, syrup, methyl cellulose, methylhydroxy benzoate, propyl hydroxybenzoate, talc, magnesium stearate and mineral oil, but is not limited thereto. The vaccine composition of the present invention may further contain a lubricant, a wetting agent, a sweetener, a flavor, an emulsifier, a suspending agent, a preservative or the like, in addition to the ingredients described above. Suitable pharmaceutically acceptable carriers and formulations are described in detail in Remington's Pharmaceutical Sciences (19th ed., 1995).

The vaccine composition of the present invention can be administered orally or parenterally. In the case of parenteral administration, the vaccine composition can be administered through intravenous injection, subcutaneous injection, intramuscular injection, intraperitoneal injection, transdermal administration or the like.

A suitable dosage of the vaccine composition of the present invention may be variably prescribed based on factors such as the formulation method, administration method, and age, body weight, gender, pathological condition, food, administration time, administration route, excretion rate and responsiveness of a patient.

The vaccine composition of the present invention may be prepared in a single-dose form or may be embedded into a multi-dose vial by formulating using a pharmaceutically acceptable carrier and/or excipient according to a method that can be easily implemented by a person having ordinary skill in the art to which the present invention pertains. At this time, the formulation may be in the form of a solution, suspension or emulsion in an oil or aqueous medium, or in the form of an extract, powder, granule, tablet or capsule, and may additionally contain a dispersant or a stabilizer.

Hereinafter, the present invention will be described in more detail with reference to the following examples. However, it will be obvious to those skilled in the art that these examples are provided only for illustration of the present invention and should not be construed as limiting the scope of the present invention.

Preparation Example: Preparation of Immune Modulator (EG-IM)

1. Preparation of Dried Strain Cell

*E. coli* was cultured with shaking at 80 rpm or less in 30 g/L of a TSB (Tryptic soy broth, Difco) medium at 37° C. for 20 hours, and the cells were collected using a centrifuge. The collected cells were mixed with ethanol and centrifuged to obtain a precipitate. Then, acetone was added to the obtained precipitate, thoroughly mixed and then centrifuged to obtain a precipitate. Ethyl ether was added to the obtained precipitate, thoroughly mixed and then centrifuged to obtain a precipitate. The obtained precipitate was dried in a drying oven at 60° C. to prepare dried bacteria cells.

2. LOS Extraction

After measuring the weight of the dried bacteria cells, 7.5 mL of a PCP (phenol, chloroform, petroleum ether) extract solution was added per 1 g of the weight to separate LOS from the bacteria cells. The organic solvent was removed at a high temperature from the LOS extract obtained by the method using a rotary evaporator. The remaining extract was centrifuged at a high temperature to obtain a precipitate, and the precipitate was washed with ethyl ether. Purified water was then added thereto to form a precipitate. The formed precipitate was centrifuged and separated from the supernatant, and the remaining precipitate was washed with ethanol and thus collected. The precipitate was thoroughly dried in a high-temperature drying oven and the precipitate was dissolved in purified water to extract LOS.

3. Removal of LOS Toxicity

After determining the content of the LOS extract, the concentration of the LOS extract was adjusted to 3 mg/mL and the LOS extract was mixed with 0.2 N NaOH at a volume ratio of 1:1. The reaction was allowed to proceed in a constant-temperature water bath at 60° C. for 120 minutes and stirred using a vortex mixer for 5 seconds every 10 minutes. Then, 1N acetic acid was added thereto in an amount of about ⅕ of the initial amount of 0.2 N NaOH. Then, EG-IM, an immune modulator, was obtained through ethanol precipitation.

4. Quantification and Identification of LOS and EG-IM

The contents of LOS and EG-IM were measured by KDO (2-keto-3-dioxyoctonate) assay using 2-thiobarbituric acid, the concentrations thereof were measured, and LOS and EG-IM were separated based on size through SDS-PAGE and identified by silver staining, and are shown in FIG. 1. FIG. 1 in image A shows the results of identification of the extracted LOS through electrophoresis and silver staining. FIG. 1 in image B shows a result indicating that the size of EG-IM decreases based on LOS extracted by degradation of lipid A when treating LOS with an alkali, wherein M represents a marker (SeeBlue® Plus 2 prestained standard, Invitrogen, LC5952), lane 1 represents LOS extracted before deacylation, and lane 2 represents EG-IM, deacylated LOS.

Example 1: Structural Analysis of Immune Modulator (EG-IM)

Figure 2:
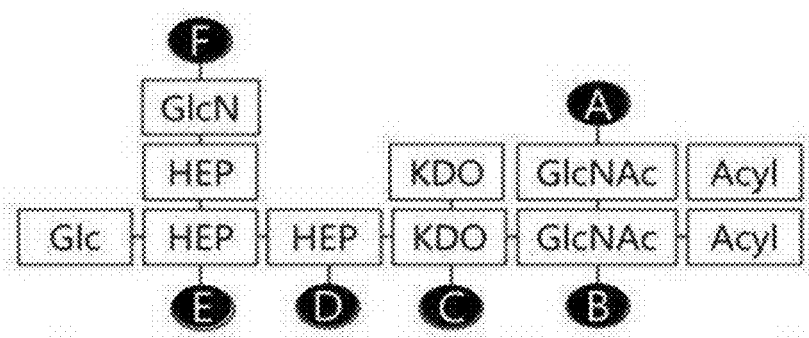
FIG. 2 shows the structure of the EG-immune modulator (EG-IM) according to the present invention, wherein Glc is glucose, GlcN is glucosamine, HEP is heptose, KDO is 2-keto-3-deoxy-octonate, GlcNAc is N-acetylglucosamine, and A to F are positions to which phosphates can be bonded.

The purified sample was suitably diluted with purified water. A CU18 reverse-phase column (ACQUITY BEH300 C18 1.7 um 2.1×150 mm) was mounted on the instrument (UPLC, Water) and the sample was then separated at a concentration gradient of 35 to 95% using mobile phase A (50 mM ammonium formate pH 4.5) and mobile phase B (100% acetonitrile). MS analysis and MS/MS analysis were conducted with a mass spectrometer (VELOS PRO, Thermo). Molecules having a molecular weight of 100 to 3,000 m/z were analyzed. After MS analysis, the identified molecules having a molecular weight of 50 to 2,000 m/z were analyzed once again. A molecule having a molecular weight of 2,372 m/z was identified as a major ingredient, and a structural schematic diagram obtained by analyzing each peak is shown in FIG. 2.

Preparation Example 2: Preparation of EG-IM-Containing Liposome (Liposomal EG-IM)

1. Preparation of EG-IM Solution and MPL Solution (1) Preparation of 0.3% (v/v) Triethylamine Solution Containing EG-IM A 0.3% (v/v) triethylamine solution containing 1 mg/mL of EG-IM was prepared and stored at −20° C.

(2) Preparation of 10% (w/v) Sucrose Solution Containing EG-IM

A 10% (w/v) sucrose solution containing 1 mg/mL of EG-IM was prepared.

(3) Preparation of 0.3% (v/v) Triethylamine Solution Containing MPL 5 mL of 0.3% (v/v) triethylamine was added to a vial containing 5 mg of MPL, vortexed vigorously and sonicated for 10 minutes to prepare a homogeneous MPL solution. The prepared solution was aliquoted at 1 mg/mL into silicone tubes and stored at −20° C.

2. Preparation of Liposomal EG-IM (1) Lipid Dissolution and Preparation of Sample by Mixing with Glycolipid A 1 mg/mL DMPC or DOTAP solution was prepared using tert-butylalcohol as a solvent and then vortex-mixed. 1 mL of the prepared DMPC solution and 1 mL of the DOTAP solution were dispensed into vials to prepare a lipid mixed solution in which DMPC and DOTAP were mixed at a ratio of 1:1 (v/v).

The lipid mixed solution was mixed with 0.3% (v/v) triethylamine containing EG-IM to prepare a lipid mixed solution containing 6 mol %, 3 mol % or 1 mol % of EG-IM, and the lipid mixed solution was mixed with 0.3% (v/v) triethylamine containing MPL to prepare a lipid mixed solution containing 6 mol %, 3 mol % or 1 mol % of MPL. Then, the vial containing the lipid mixed solution was preliminarily frozen in a deep freezer at −70° C. for 1 hour and then lyophilized for 12 hours or longer to prepare a lipid mixture cake.

(2) Preparation of Liposome Through Rehydration Process 1 mL of a 10% (w/v) sucrose solution was added to a simple lipid mixture vial and a lipid mixture vial containing EG-IM or MPL in the presence of the lipid mixture cake, followed by vortex-mixing to prepare liposomes.

(3) Preparation of Sample by Simply Mixing Glycolipids with Liposomes

A 10% (w/v) sucrose solution containing EG-IM was mixed with a liposome solution at respective dosages to prepare a sample containing a simple mixture of liposome with 6 mol %, 3 mol % or 1 mol % of EG-IM.

A 0.3% (v/v) triethylamine solution containing MPL was mixed with a liposome solution to prepare a sample containing a simple mixture of liposome with 6 mol %, 3 mol % or 1 mol % of MPL.

Example 2: Analysis of Physical Properties of Liposomal EG-IM

1. Liposome Size Analysis (1) Analysis of Liposome Size Change Rate 1 mL of each of the sample of the lipid dissolution step and 1 mL of a sample obtained by simply mixing the glycolipid of Preparation Example 2-(3) with liposome were added to a cuvette, and a hydrodynamic size was measured using a dynamic light-scattering apparatus (Malvern instrument, ZSP nano) (Table 2).

TABLE 2

| Type of glycolipid | Glycolipid incorporation step | Liposome size (d, nm) Glycolipid content | | |
|---|---|---|---|---|
| | | 6 mol % | 3 mol % | 1 mol % |
| MPL | Lipid dissolution step | 355.4 ± 7.1 | 309.2 ± 3.7 | 367.9 ± 16.1 |
| | Step of simple mixing with liposome | 1538.7 ± 457.1 | 1206.1 ± 244.2 | 694.9 ± 33.2 |

TABLE 2-continued

| Type of glycolipid | Glycolipid incorporation step | Liposome size (d, nm) Glycolipid content | | |
|---|---|---|---|---|
| | | 6 mol % | 3 mol % | 1 mol % |
| EG-IM | Lipid dissolution step | 439.3 ± 6.1 | 386.1 ± 1.2 | 372.7 ± 6.0 |
| | Step of simple mixing with liposome | 829.8 ± 11.1 | 414.0 ± 43.7 | 565.7 ± 28.9 |

As a result, it was observed that MPL tended to increase in size when simply mixed with a liposome. On the other hand, EG-IM slightly increased in size, but was less than 1 μm, when prepared in a high-content/simple mixing manner, and the content and the preparation method did not affect the size change. Therefore, a liposomal EG-IM (EG-IM-containing liposome) can be prepared in a variety of forms such as encapsulation- or adsorption-type due to the small rate of change in size after preparation, and can also be prepared with a nanosize of 300 to 600 nm (<1 μm).

Figure 3:
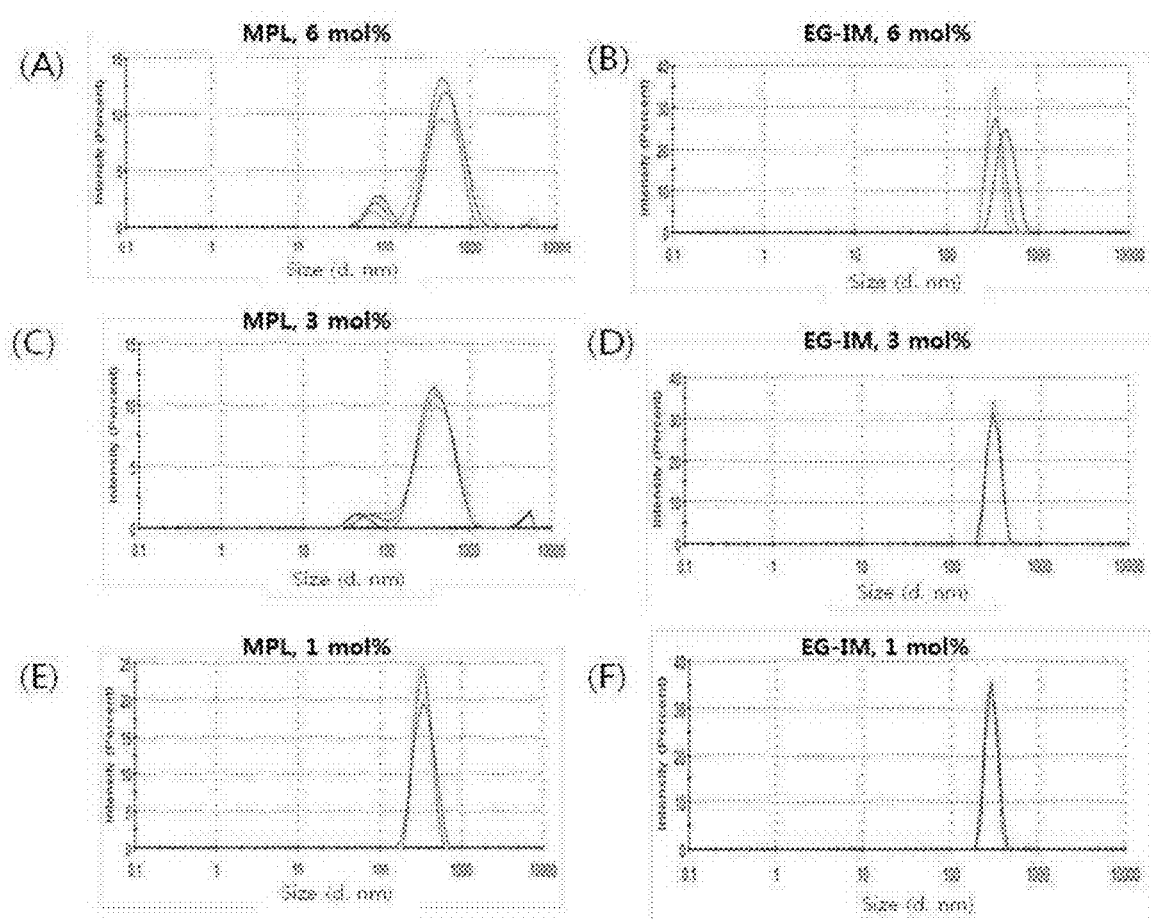
FIG. 3 is a diagram showing a liposome size distribution in a lipid-dissolution step.
Figure 4:
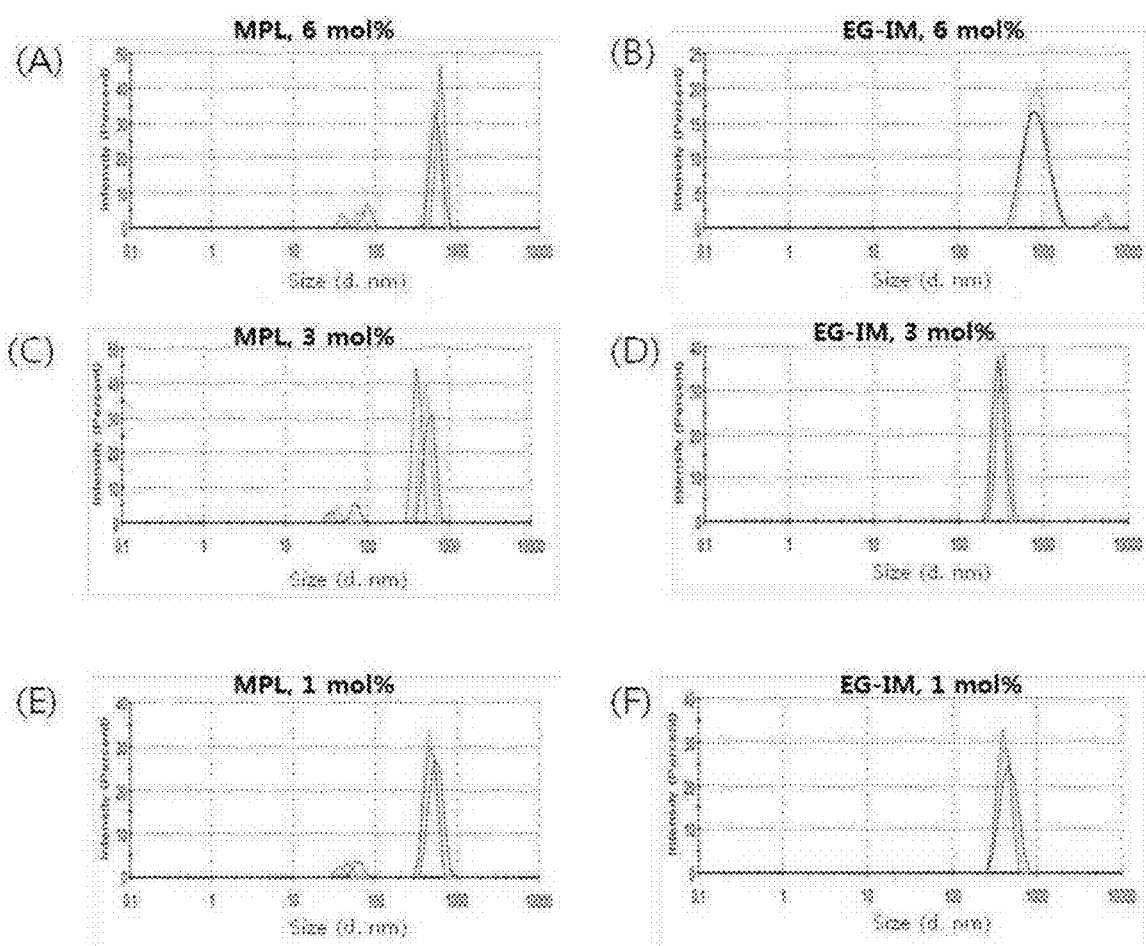
FIG. 4 is a diagram showing a liposome size distribution in a step of simply mixing glycolipid with a liposome.

(2) Analysis of Liposome Size Homogeneity 1 mL of each of the sample of the lipid dissolution step and 1 mL of a sample obtained by simply mixing the glycolipid of Preparation Example 2-(3) with liposome were added to a cuvette, and a hydrodynamic size and distribution were analyzed using a dynamic light-scattering apparatus (Malvern instrument, ZSP nano) (Table 3, FIGS. 3 and 4). FIG. 3 is a diagram showing a liposome size distribution in a lipid-solubilization step, and FIG. 4 is a diagram showing a liposome size distribution in a step of simply mixing glycolipid with a liposome.

TABLE 3

| Type of glycolipid | Glycolipid incorporation step | Liposome PDI Glycolipid content | | |
|---|---|---|---|---|
| | | 6 mol % | 3 mol % | 1 mol % |
| MPL | Lipid dissolution step | 0.405 ± 0.080 | 0.412 ± 0.030 | 0.353 ± 0.011 |
| | Step of simple mixing with liposome | 0.887 ± 0.098 | 0.793 ± 0.052 | 0.552 ± 0.020 |
| EG-IM | Lipid dissolution step | 0.271 ± 0.209 | 0.405 ± 0.019 | 0.407 ± 0.020 |
| | Step of simple mixing with liposome | 0.227 ± 0.031 | 0.402 ± 0.133 | 0.471 ± 0.016 |

As a result, it was found that the dispersibility of MPL increased depending on concentration. On the other hand, the dispersibility of EG-IM remained uniform regardless of content.

When a glycolipid was incorporated during the lipid dissolution, a liposome, in which the glycolipid was encapsulated, was formed (FIG. 3). It was found that, in the case of MPL, the size distribution of the prepared liposome was not uniform and micelles of MPL itself were formed (FIGS. 3A, 3C and 3E). On the other hand, in the case of EG-IM, it could be found that the prepared liposome was homogeneously prepared to thus form a single peak (FIGS. 3B, 3D, and 3F). Thus, it was found that EG-IM can uniformly prepare an encapsulated liposome.

Simple mixing of the liposome with glycolipid formed a liposome in which the glycolipid was adsorbed on the surface of the liposome (FIG. 4). In the case of MPL, it was found that the size distribution of the prepared liposome was not uniform (Table 3) and micelles of MPL itself were formed (FIGS. 4A, 4C and 4E). On the other hand, in the case of EG-IM, it was found that the liposome was uniformly prepared to form a single peak (FIGS. 4B, 4D and 4F). Therefore, it was found that EG-IM can uniformly prepare an adsorbed liposome as well.

2. Liposome Surface Charge Analysis 1 mL of each of the sample of the lipid dissolution step and 1 mL of a sample obtained by simply mixing the glycolipid of Preparation Example 2-(3) with a liposome were loaded on a cuvette for measuring a surface charge (zeta potential), and a surface charge was measured using a dynamic light-scattering apparatus (Malvern instrument, ZSP nano) (Table 4).

TABLE 4

| Type of glycolipid | Glycolipid incorporation step | Liposome surface charge (mV) Glycolipid content | | |
|---|---|---|---|---|
| | | 6 mol % | 3 mol % | 1 mol % |
| MPL | Lipid dissolution step | 23.7 ± 0.6 | 56.2 ± 0.6 | 57.0 ± 3.0 |
| | Step of simple mixing with liposome | 48.5 ± 1.4 | 56.9 ± 3.4 | 57.8 ± 1.6 |
| EG-IM | Lipid dissolution step | 54.7 ± 1.3 | 59.2 ± 1.0 | 55.2 ± 2.7 |
| | Step of simple mixing with liposome | 57.5 ± 1.3 | 56.5 ± 2.3 | 55.1 ± 2.6 |

As a result, in the case of EG-IM, the surface charge remained uniform at 55 mV regardless of content. On the other hand, in the case of MPL, the surface charge decreased sharply when mixed at a high content of 6 mol %.

Example 3: Analysis of Liposomal EG-IM Mechanism

1. Effects of Liposomal EG-IM on Immune Cell Proliferation and Cytotoxicity Mitigation (1) Effect of Liposomal EG-IM on Immune Cell Proliferation Mouse macrophage cell line (J774A.1) cells were treated with EG-IM (0.025, 0.05, 0.1, 0.5, or 1.0 μg/ml) and various concentrations of liposome (1.25, 2.5, 5, 25 or 50 μg/ml as a cationic lipid), or a mixture thereof. 24 hours after treatment of the cells with a test reagent, the cells were treated with a CCK-8 solution and allowed to react for one hour. After completion of the reaction, the cell culture was collected, absorbance was measured at 450 nm, and the cell viability of each test group was calculated based on 100% of an absorbance of the group treated with the culture solution (negative control group).

NP is a group treated with a liposome alone, NP+EG-IM is a group treated with a simple mixture of an EG-IM and a liquid liposome, and NP/EG-IM is a formulation obtained by lyophilizing a mixture of a liposome and an EG-IM.

NP-A represents a DDA:DOPC liposome, NP-B represents a DOTAP:DMPC liposome, NP-C represents a DOTAP:DMPC:squalene liposome and NP-D represents a DOTAP:DMPC:tricaprin liposome.

Figure 5:
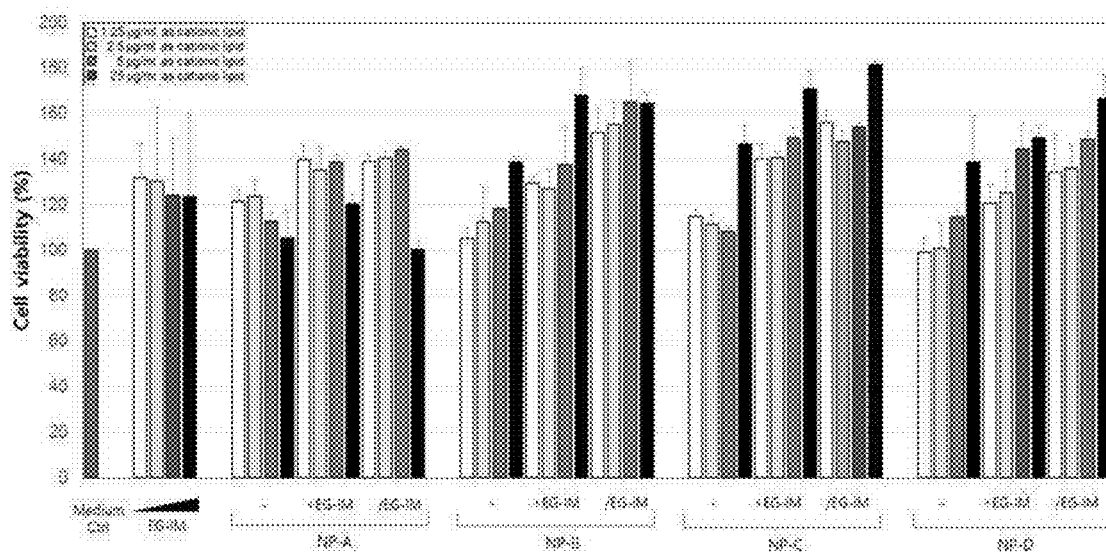
FIG. 5 is a graph showing the effect of liposomal EG-IM on the proliferation of immune cells.

As a result, it was found that when EG-IM was mixed with various concentrations of cationic liposome, the growth of immune cells was increased (FIG. 5).

(2) Effect of Liposomal EG-IM on TNF-α Secretion

Mouse macrophage cell line (J774A.1) cells were treated with EG-IM (0.025, 0.05, 0.1, 0.5, or 1.0 µg/ml) and various concentrations of liposome (1.25, 2.5, 5, 25 or 50 µg/ml as a cationic lipid), or a mixture thereof The cells were treated with a test reagent and cultured for 24 hours, and the TNF-α cytokine secretion level in the cell culture media was measured by sandwich ELISA.

NP is a group treated with a liposome alone, NP+EG-IM is a group treated with a simple mixture of an EG-IM and a liquid liposome, and NP/EG-IM is a formulation obtained by lyophilizing a mixture of a liposome and an EG-IM.

NP-A represents a DDA:DOPC liposome, NP-B represents a DOTAP:DMPC liposome, NP-C represents a DOTAP:DMPC:squalene liposome and NP-D represents a DOTAP:DMPC:tricaprin liposome.

Figure 6:
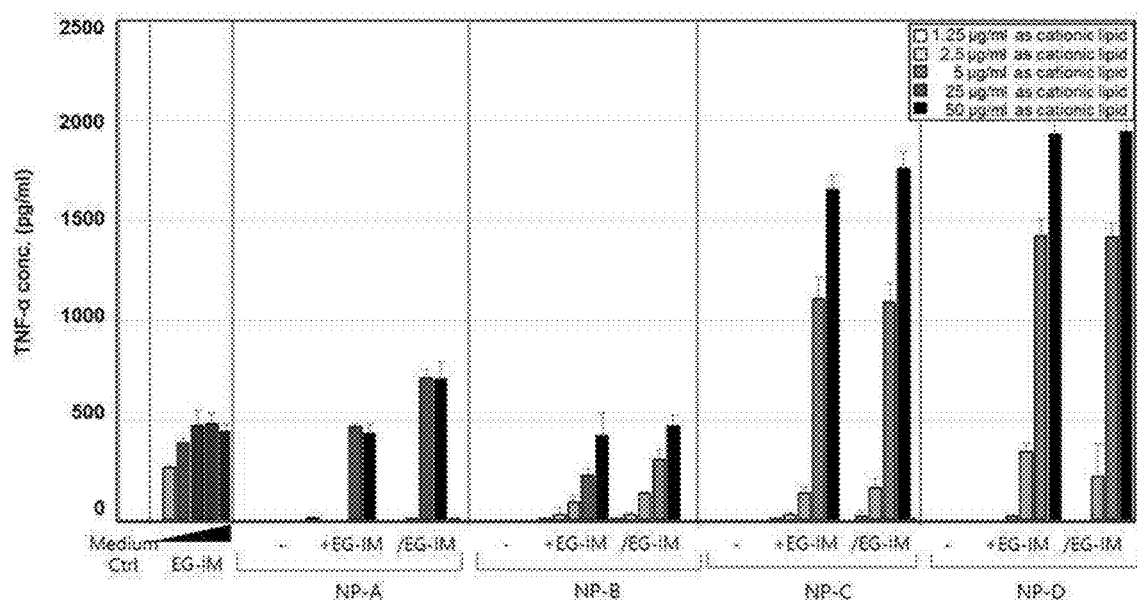
FIG. 6 is a graph showing the effect of liposomal EG-IM on induction of TNF secretion.

As a result, it was found that when EG-IM was mixed with various concentrations of cationic liposome, TNF-α secretion activity was induced (FIG. 6).

(3) Effect of Liposomal EG-IM on Cytotoxicity Mitigation

Cationic liposomes are generally known to cause cytotoxicity. Whether or not the prepared liposomal EG-IM had the effect of mitigating cytotoxicity of the cationic liposome by EG-IM was determined. The cytotoxicity of liposomal EG-IM was measured using human fibroblast MRC-5 cells. The cytotoxicity of the prepared liposome, the cationic liposome composed of DDA:DMPC, was evaluated depending on the presence or absence of cholesterol and homogenization method, and the presence or absence of the immunostimulatory substance, EG-IM. MRC-5 cells were stimulated through treatment of each substance at different concentrations and cytotoxicity was evaluated through an MTT assay.

A represents a liposome containing no cholesterol, B represents a liposome containing cholesterol, 1 represents a liposome homogenized group using an extruder, and 2 represents a liposome homogenized group using a sonicator.

Figure 7:
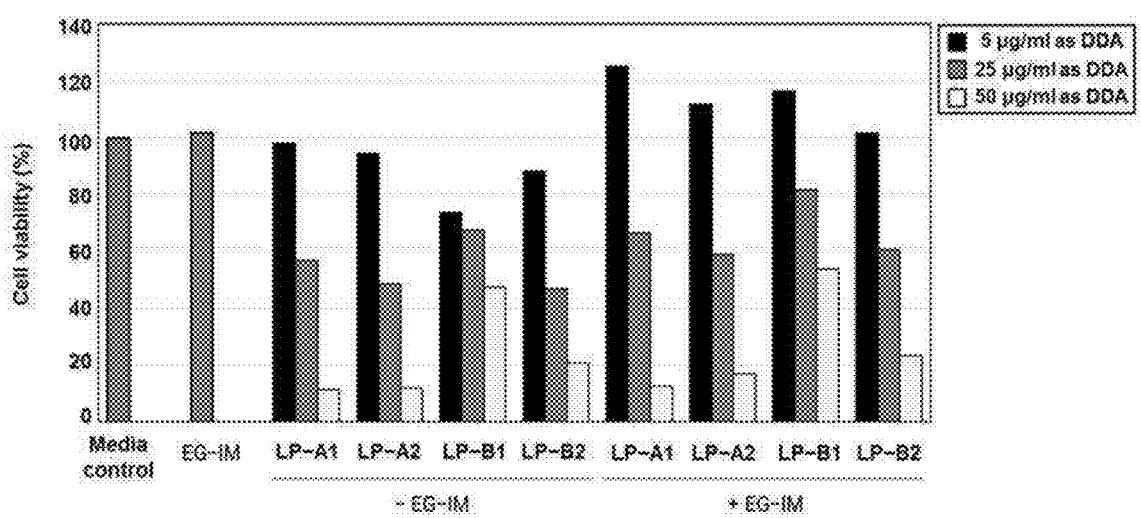
FIG. 7 is a graph showing the effect of liposomal EG-IM on cytotoxicity mitigation.

As a result, it was found that the cytotoxicity, which was expressed in a DDA:DMPC concentration-dependent manner was alleviated by an EG-IM mixture (FIG. 7).

2. Formation Mechanism of Vaccine Containing Liposomal EG-IM: Adsorption by Electrostatic Attraction A liposome (LP), a recombinant VZV gE protein and an EG-IM were mixed and centrifuged (4° C., 100,000×g, 1 hr) in order to determine whether or not the formation mechanism of a liposomal EG-IM vaccine was adsorption by electrostatic attraction. After separating the supernatant (S) and the precipitate (pellet, P), the precipitate was completely suspended through sonication in the same volume of PBS as the supernatant. Samples with the same volume were electrophoresed and then subjected to silver staining.

Figure 8:
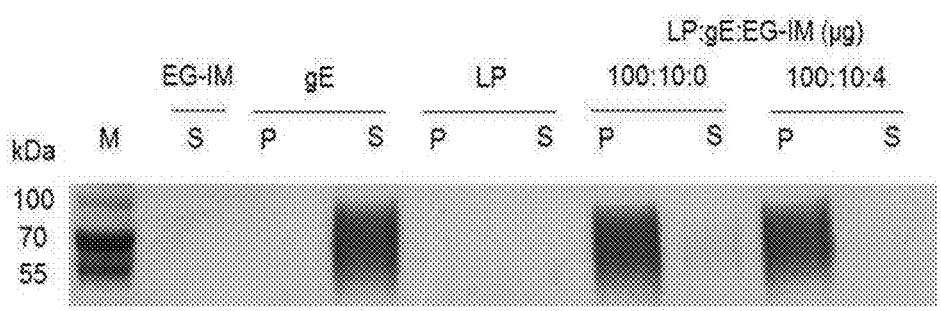
FIG. 8 shows a result demonstrating that the formation of a vaccine containing liposomal EG-IM is formed by electrostatic attraction, wherein LP represents a liposome, S represents a supernatant and P represents a precipitate (pellet).

As a result, when the recombinant VZV gE protein alone was subjected to ultracentrifugation, the recombinant gE protein was detected in the supernatant. However, in the case of the liposomal EG-IM vaccine (LP:gE:EG-IM mixture), the recombinant gE protein was detected from the precipitate (FIG. 8). The recombinant gE protein was considered to be observed in the precipitate because the liposome and the recombinant gE protein were adsorbed.

3. Immunological Effect of Vaccine Containing Liposomal EG-IM

The liposomal EG-IM was administered to 6-week-old female BALB/c mice via an intramuscular route, and then the cells were removed from the muscle tissues on the injection site at 3 hours and 24 hours after administration. In order to characterize the immune cells of the separated cells, the cells were immunostained using anti-CD11b Ab (FITC), anti-CD11c Ab (FITC), anti-Ly6C Ab (PE), anti-Ly6G Ab (PE), anti-F4/80 Ab (PE), anti-MHCII Ab (PE) and anti-CD3 Ab (PE), and were analyzed by flow cytometry.

Figure 9:
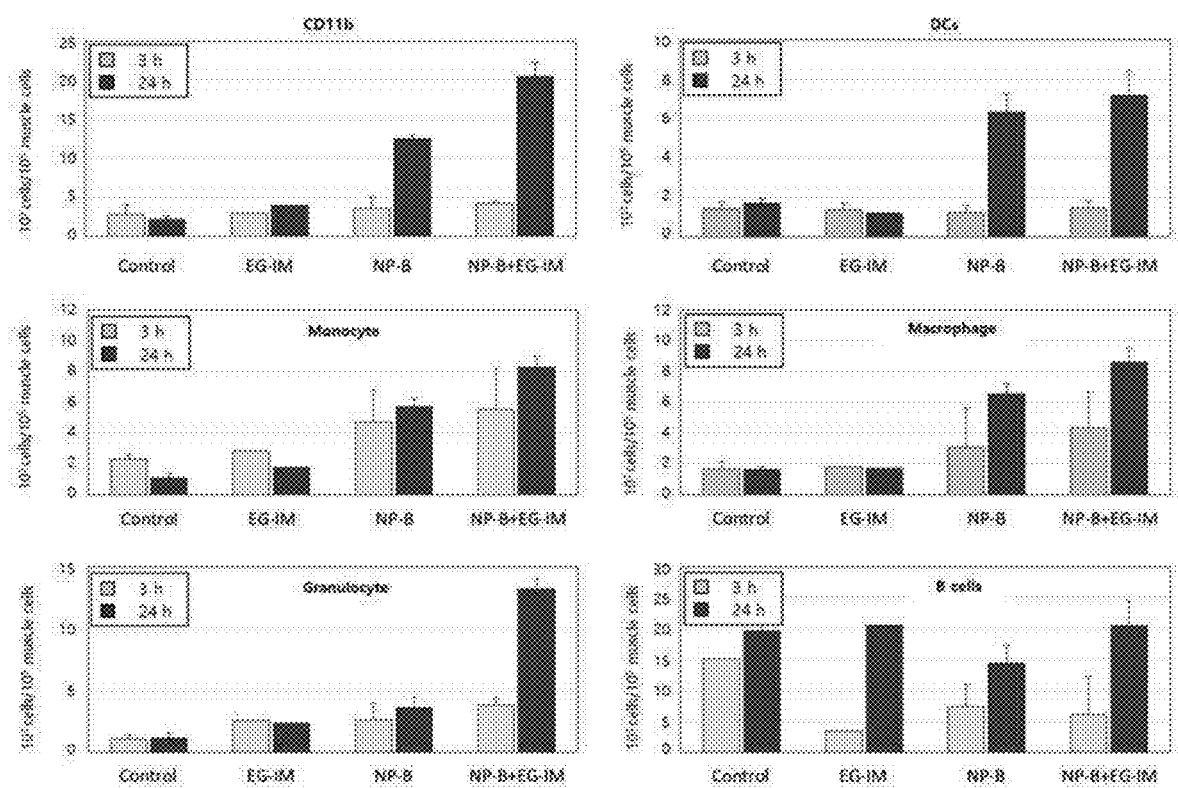
FIG. 9 is a graph showing the immune cell recruiting effect of liposomal EG-IM.

As a result, it was found that the migration of CD11b+ immune cells (monocytes, granulocytes), DCs, monocytes, macrophages and granulocytes was increased by the liposomal EG-IM on the site of injection (FIG. 9). This indicates that immune cell recruiting is initiated by the liposomal EG-IM, that the innate immune response may be induced by the liposomal EG-IM, and that the liposomal EG-IM uptake by immune cells may be increased.

(2) Uptake Effect of Vaccines Containing Liposomal EG-IM

The gE protein was labeled with a fluorescent substance (Alexa647), dendritic cells (DCs) were treated with the gE protein, and DCs in which fluorescence was detected were analyzed by flow cytometry.

Figure 10:
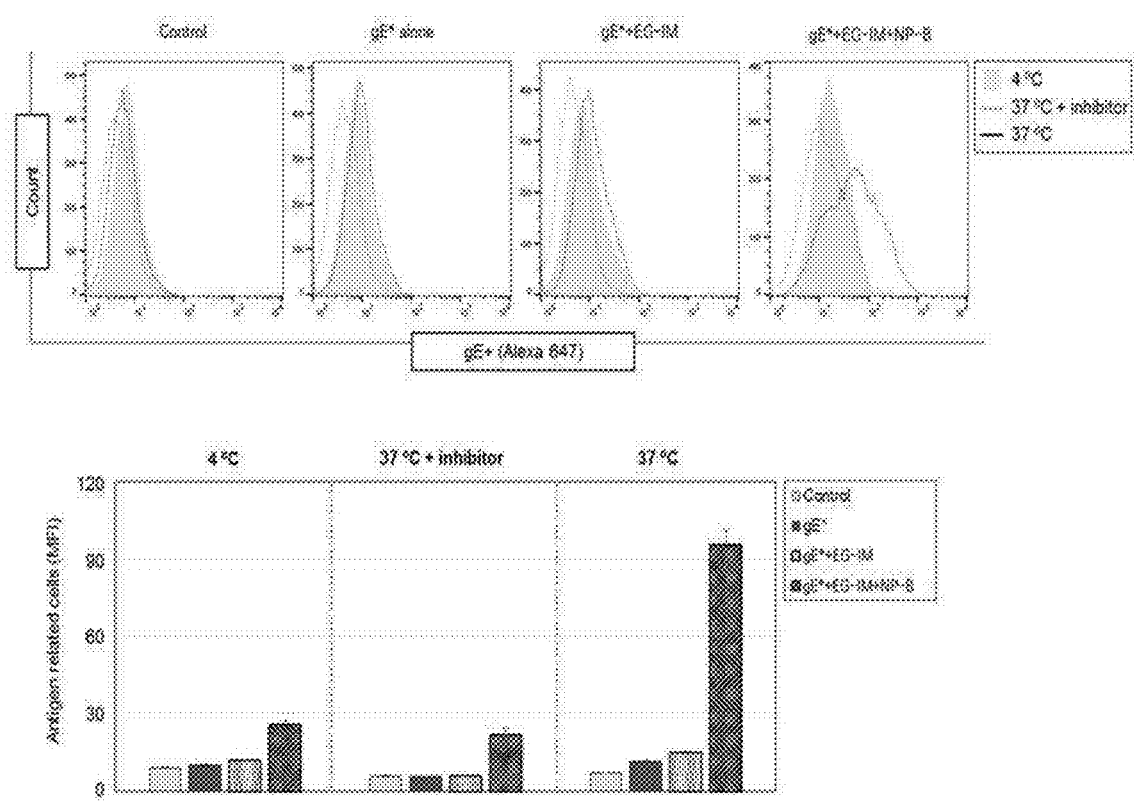
FIG. 10 shows the results of analysis of an uptake effect of a vaccine containing liposomal EG-IM by flow cytometry and FIG. 11 includes graphs A-D showing the uptake effect by monocytes, in which graph A shows the result of analysis of fluorescence-labeled gE protein-specific cells in dLN, graph B shows the result of analysis of fluorescence-labeled gE protein-specific cells in muscle tissue, graph C shows the result of measurement of fluorescence-labeled gE protein-specific monocytes in dLN, and graph D shows the result of measurement of fluorescence-labeled gE protein-specific monocytes in muscle tissue.

As a result, fluorescent DCs were not observed when the gE protein or EG-IM was used alone, but fluorescent DCs were detected when the liposomal EG-IM was used as an adjuvant system (FIG. 10). This indicates that the vaccine containing liposomal EG-IM increases antigen uptake efficiency of DCs.

Figure 11:
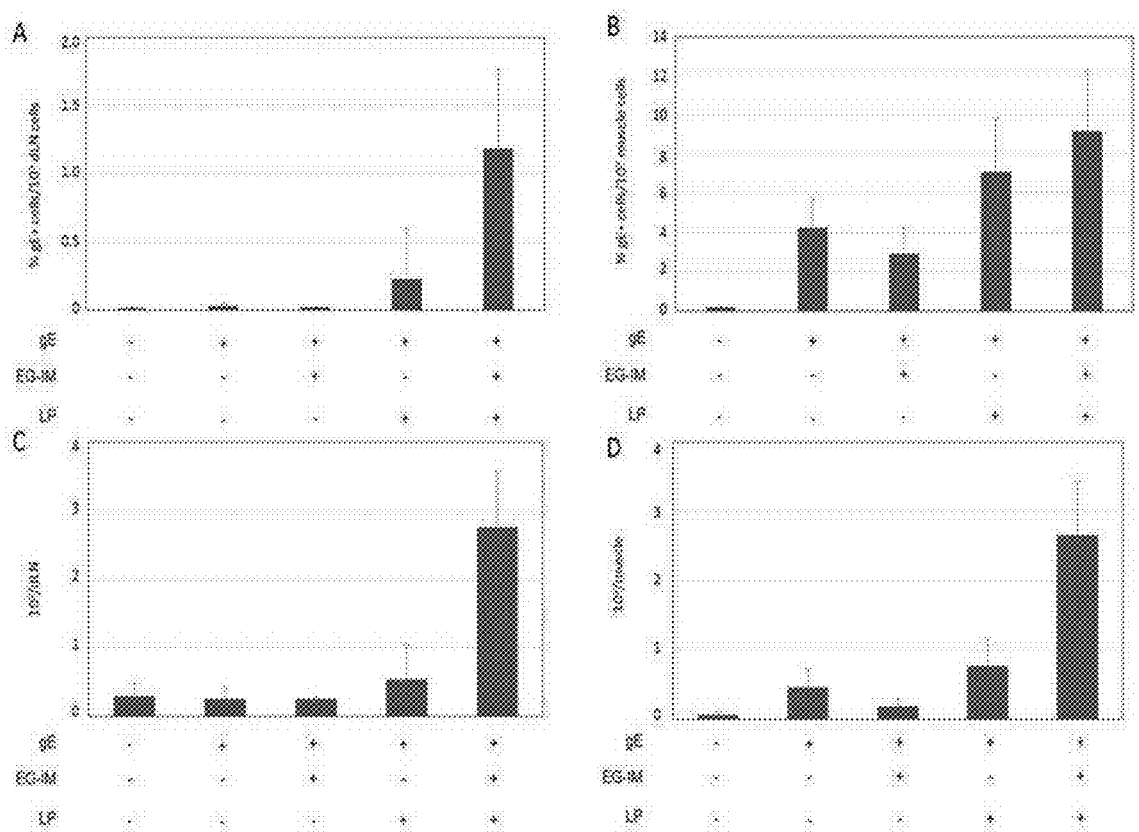
Figure 12:
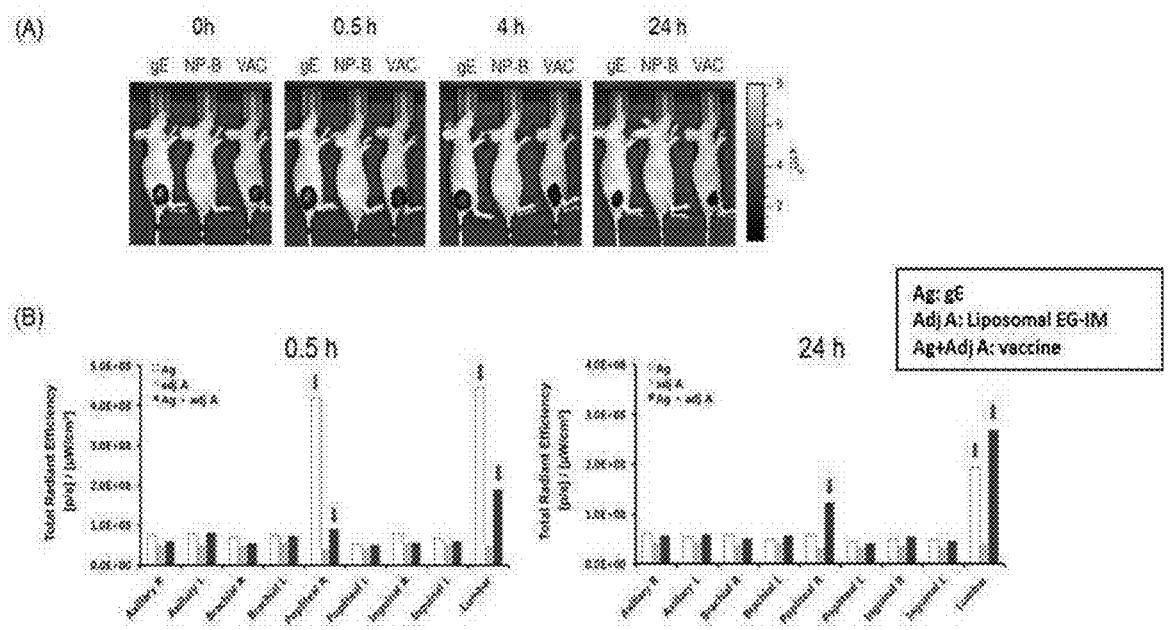
FIG. 12 shows a depot effect of a vaccine containing liposomal EG-IM.

In addition, the recombinant VZV gE protein was labeled with a fluorescent substance (Alexa647) and then mixed with the liposomal EG-IM to prepare a vaccine. The prepared vaccine was administered to the mouse thigh deltoid, and 4 hours and 24 hours after administration, surface marker fluorescence staining of immune cells was performed using draining lymph node (dLN) and muscle tissue, and analyzed through flow cytometry. The analysis results are shown in FIG. 11. FIG. 11 in graph A shows the results of analysis of fluorescence-labeled gE protein-specific cells in dLN, FIG. 11 in graph B shows the results of analysis of fluorescence-labeled gE protein-specific cells in muscle tissue, FIG. 11 in graph C shows the results of measurement of fluorescence-labeled gE protein-specific monocytes in dLN, and FIG. 11 in graph D shows the results of measurement of fluorescence-labeled gE protein-specific monocytes in muscle tissue.

As a result, when the liposomal EG-IM was used as an adjuvant system, cells were recruited into dLN and muscle tissue, and the uptake of the vaccine by monocytes was actively induced, as compared to the case where the recombinant VZV gE protein or EG-IM was used alone (FIG. 11).

(3) Depot Effect of Vaccine Containing Liposomal EG-IM

The gE protein was labeled with a fluorescent substance (Alexa647) and mixed with liposomal EG-IM to prepare a vaccine. 30 minutes and 24 hours after the prepared vaccine was administered to the mouse thigh deltoid, in vivo fluorescence images were taken (A) and the fluorescence of lymph nodes separated from the mice was measured (B).

As a result, fluorescence was detected at an injection site for up to 24 hours, both in the case where a gE protein (antigen) was administered alone and in the case where the vaccine containing liposomal EG-IM (VAC) was administered. Fluorescence was analyzed at each lymph node. As a result, fluorescence was detected at a relatively high intensity in the lumbar and muscle popliteus. When the antigen was administered alone, the fluorescence intensity was halved after 24 hours, but when the vaccine containing liposomal EG-IM was administered, the fluorescence sensitivity was not halved (FIG. 12). This indicates that the vaccine containing liposomal EG-IM enhanced a depot effect.

Example 4. Analysis of Immunogenicity of Liposomal EG-IM in Zika Vaccine

A recombinant Zika virus envelope protein was used to identify the immunogenicity enhancement effect of the liposomal EG-IM in a Zika vaccine. A mixture of a recombinant Zika virus envelope glycoprotein, and alum (aluminum hydroxide; Brenntag, Germany), an EG-IM and a liposomal EG-IM as a variety of immune adjuvants was intramuscularly administered to 6-week-old BALB/c mice (SLC, Japan) twice at intervals of two weeks. Regarding the amounts of administration, the recombinant Zika virus envelope glycoprotein was administered in 2 μg/mouse, the alum was administered in 25 μg/mouse, the EG-IM was administered in 0.5 μg/mouse, and the liposomal EG-IM was administered in 25 μg/mouse. Two weeks after the final administration, mice were anesthetized, and spleen tissues were extracted and separated into single cells. The separated spleen cells were stimulated with 5 μg/mL of an antigen and cultured for 72 hours. Then, the level of secreted IFN-γ cytokine in the cell culture media was analyzed using an ELISA kit (R&D systems, Millipore).

Figure 13:
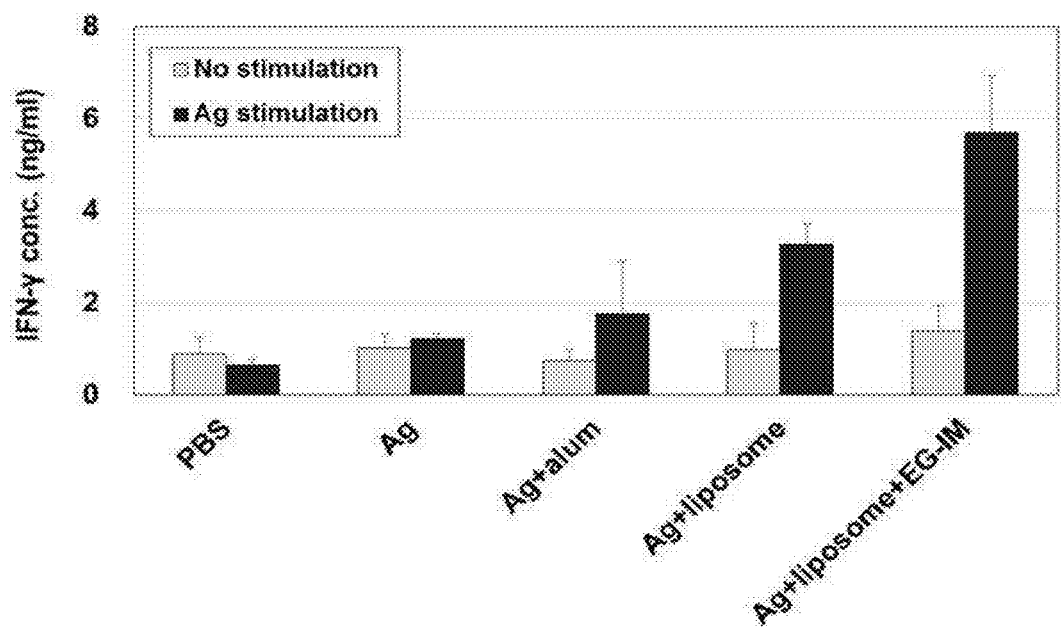
FIG. 13 shows a Zika virus antigen-specific antibody titer of a Zika virus vaccine containing liposomal EG-IM.

As a result, a test group using the liposomal EG-IM enhanced IFN-γ secretion, as compared to a test group using alum alone or liposome alone (FIG. 13). Thus, it was found that the Zika vaccine containing the liposome EG-IM has excellent ability to induce cellular immunity.

Example 5: Analysis of Immunogenicity of Liposomal EG-IM in Japanese Encephalitis Virus Vaccine A Japanese encephalitis virus (JEV) antigen was used in order to identify the immunogenicity enhancement effect of the liposomal EG-IM in a Japanese encephalitis virus (JEV) vaccine. A mixture of an inactivated JEV antigen, and an EG-IM and a liposomal EG-IM as an immune adjuvant was intramuscularly administered to 6-week-old BALB/c mice (SLC, Japan) twice at intervals of two weeks. Regarding the amounts of administration, the inactivated JEV antigen was administered in 0.5 μg/mouse, the EG-IM was administered in 0.5 μg/mouse, and the liposomal EG-IM was administered in 25 μg/mouse.

1. Measurement of JEV Antigen-Specific Antibody Titers

Four weeks after the last administration, mice were anesthetized, and cardiac blood was collected therefrom to prepare a blood sample. After immunization, an end-point dilution enzyme-linked immunosorbent assay method was used in order to measure the JEV antigen-specific antibody titers in sera. The JEV antigen was diluted to a concentration of 1 μg/ml, coated on a 96-well plate at 100 μl/well (4° C., overnight) and blocked with 300 μl of 1% BSA (bovine serum albumin) (room temperature, 1 hour). After blocking, washing three times with PBS containing 0.05% Tween-20, and the serum obtained after immunization was diluted by 10-fold serial dilution, and 100 μl of each diluted serum was reacted (37° C., 2 hours). In order to identify the JEV antigen-specific antibody, a horseradish-peroxidase-conjugated anti-mouse IgG antibody (Jackson, 115-035-003), a horseradish-peroxidase-conjugated anti-mouse IgG1 antibody (Serotec, STAR132P), and a horseradish-peroxidase-conjugated anti-mouse IgG2 antibody (Serotec, STAR133P) were allowed to react, then TMB (tetramethylbenzidine, BD Bio science, 55555214) was added thereto, and the reaction was stopped with 1N $H_2SO_4$. Test results were obtained by measuring absorbance at 450 nm and measuring titers of IgG, IgG1 and IgG2a antibodies.

Figure 14:
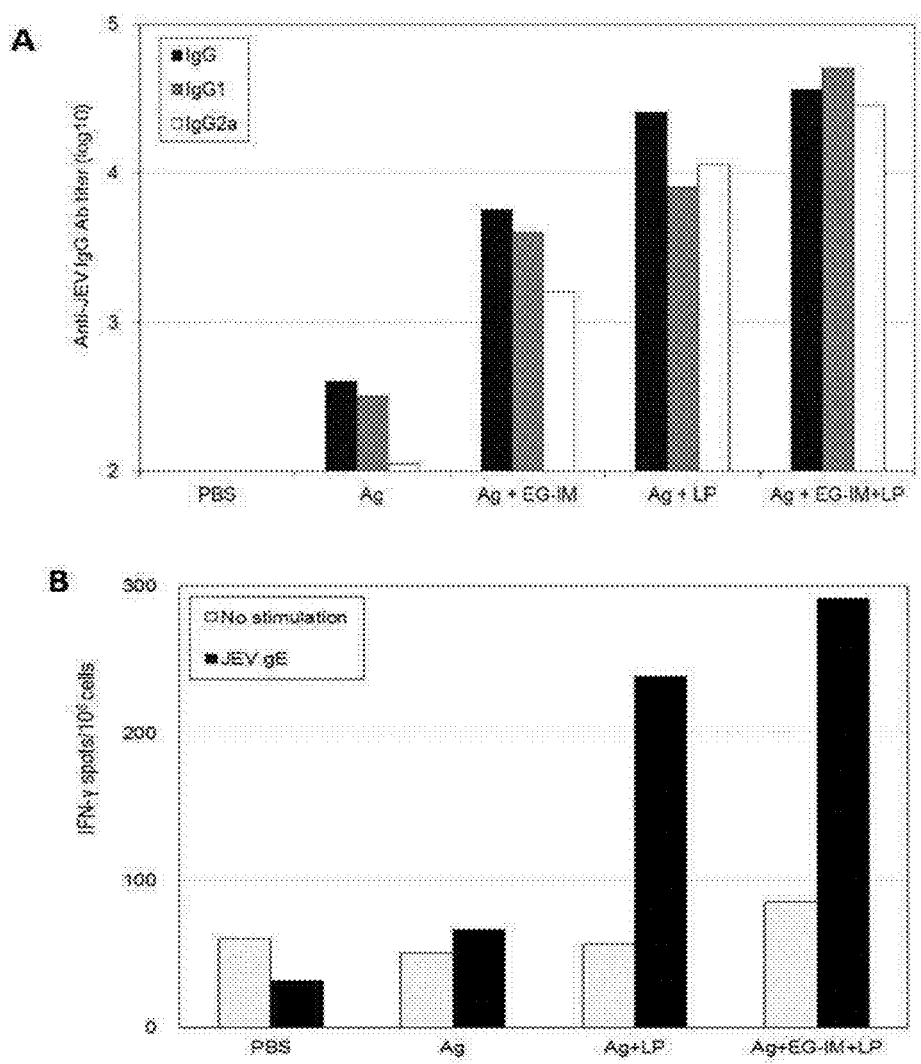
FIG. 14 in graph A shows a JEV-specific-antibody titer of a Japanese encephalitis vaccine containing liposomal EG- IM, and in graph B shows the amount of IFN-γ cytokine secreted after administration of the Japanese encephalitis vaccine.

As a result, in the test group using liposomal EG-IM, the production of the JEV antigen-specific IgG, IgG1 antibody, and IgG2a antibody levels were increased, as compared to the test group using EG-IM alone or liposome alone (FIG. 14 in graph A). Thus, the Japanese encephalitis vaccine of the present invention containing liposomal EG-IM shows excellent immune efficacy, that is, vaccine efficacy.

2. Cytokine Analysis 14 weeks after the final administration, mice were anesthetized, spleen tissues were extracted and separated into single cells, and the cells were stimulated with 1 μg/ml of a recombinant JEV glycoprotein. After 24 hours, cells secreting IFN-γ cytokine were analyzed by ELISPOT ELISA (Millipore).

As a result, the test group using liposomal EG-IM increased the number of cells secreting IFN-γ cytokine, as compared to the test group using a liposome alone (FIG. 14 in graph B). Thus, the Japanese encephalitis vaccine containing liposomal EG-IM has excellent ability to induce cellular immunity.

Example 6: Analysis of Immunogenicity of Liposomal EG-IM in Tuberculosis Vaccine As a recombinant tuberculosis antigen, Ag85A, ESAT-6, or HspX alone, or a mixture of these three antigens was used in order to identify the immunogenicity enhancement effect of the liposomal EG-IM in a tuberculosis (TB) vaccine. A mixture of the recombinant tuberculosis antigen and an EG-IM and a liposomal EG-IM as immune adjuvants was intramuscularly administered to 6-week-old BALB/c mice (SLC, Japan) three times at intervals of two weeks. Regarding the amounts of administration, the recombinant tuberculosis antigen was administered in 5 μg/mouse, the EG-IM was administered in 0.5 μg/mouse, and the liposomal EG-IM was administered in 250 μg/mouse.

1. Measurement of TB Antigen-Specific Antibody Titer

Three weeks after the last administration, mice were anesthetized, and cardiac blood was collected therefrom to prepare a blood sample. An end-point dilution enzyme-linked immunosorbent assay method was used in order to measure the titer of TB antigen-specific antibody titers in sera. Test results were obtained by measuring an absorbance at 450 nm and measuring the titer of the IgG antibody in blood collected after immunization.

Figure 15:
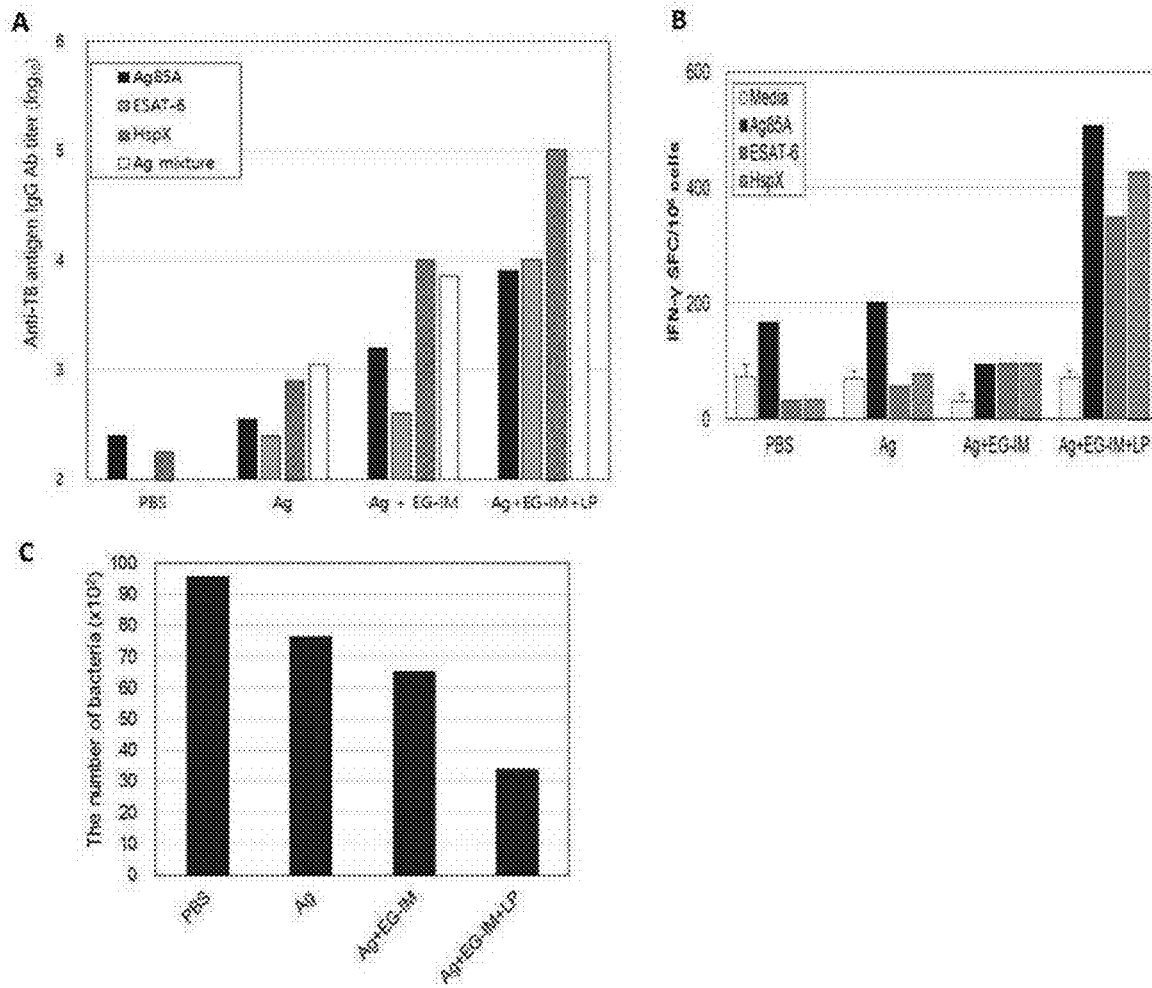
FIG. 15 in graph A shows a TB-specific antibody titer of a tuberculosis vaccine containing liposomal EG-IM, in graph B shows the amount of IFN-γ cytokine secreted after administration of a tuberculosis vaccine, and in graph C shows the result of analysis of the bactericidal effect of a tuberculosis vaccine containing liposomal EG-IM.

As a result, when Ag85A, ESAT-6, or HspX alone, or a mixture of these three antigens was used, in the test group using liposomal EG-IM, production of the recombinant TB antigen-specific IgG antibody levels were increased, as compared to the test group using EG-IM alone (FIG. 15 in graph A). Thus, the tuberculosis vaccine of the present invention containing the liposomal EG-IM exhibits excellent immune efficacy, that is, vaccine efficacy.

2. Cytokine Analysis

Three weeks after the final administration, mice were anesthetized, spleen tissues were extracted and separated into single cells, and the cells were stimulated with 1 μg/ml of a recombinant TB gE protein and cultured for 24 hours. Then, cells secreting IFN-γ cytokine were analyzed by ELISPOT ELISA (Millipore).

As a result, in all cases where the Ag85A, ESAT-6, or HspX antigen was used, the test group using the liposomal EG-IM increased the number of cells secreting IFN-γ, as compared to the test group using EG-IM alone (FIG. 15 in graph B). Thus, the tuberculosis vaccine of the present invention containing the liposomal EG-IM exhibits ability to induce cellular immunity.

3. Analysis of Bactericidal Effect

Spleen cells from immunized mice were co-cultured with BCG-infected macrophages. Seven days after culture, the cells were recovered, lysed and plated on a Middlebrook 7H11 Bacto agar plate (Difco) containing Middlebrook OADC Enrichment (Difco). After culturing at 37° C. for 4 weeks, the number of the produced bacterial colonies was counted.

As a result, it was found that the test group using the liposomal EG-IM had an excellent BCG bactericidal effect, as compared to the test group using the EG-IM alone (FIG. 15 in graph C).

Example 7: Analysis of Immunogenicity of Liposomal EG-IM in Pertussis Vaccine

An acellular pertussis (aP) vaccine antigen was used in order to identify the immunogenicity enhancement effect of the liposomal EG-IM in a pertussis vaccine. A mixture of the acellular pertussis (aP) vaccine antigen and an EG-IM, a liposome and a liposomal EG-IM as immune adjuvants was intramuscularly administered to 6-week-old BALB/c mice (SLC, Japan) twice at intervals of two weeks. Regarding the amounts of administration, the aP antigen was administered in 5 μg/mouse, the liposome was administered in 25 μg/mouse, the EG-IM was administered in 0.5 μg/mouse, and the liposomal EG-IM was administered in 25 μg/mouse.

1. Measurement of aP Antigen-Specific Antibody Titer

Two weeks after the last administration, mice were anesthetized, and cardiac blood was collected therefrom to prepare a blood sample. An end-point dilution enzyme-linked immunosorbent assay method was used in order to measure the aP antigen-specific antibody in sera. Test results were obtained by measuring an absorbance at 450 nm and measuring the IgG antibody titer of the IgG antibody in blood collected after immunization.

Figure 16:
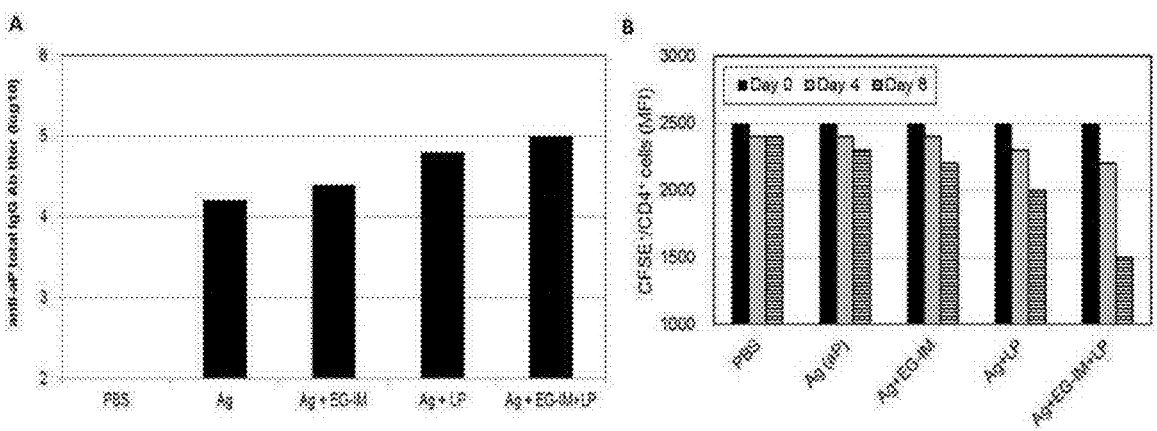
FIG. 16 in graph A shows a aP-specific antibody titer of a pertussis vaccine containing liposomal EG-IM, and in graph B shows the result of analysis of CD4+ T cell proliferation by a pertussis vaccine.

As a result, in the test group using the liposomal EG-IM, production of the aP antigen-specific IgG antibody level was increased, as compared to the test group using the EG-IM or liposome alone (FIG. 16 in graph A). Thus, the pertussis vaccine of the present invention containing the liposomal EG-IM exhibits excellent immune efficacy, that is, vaccine efficacy.

2. CD4 T Cell Growth Assay

Two weeks after the final administration, mice were anesthetized and spleen tissues were extracted, stimulated with 5 μg of an aP antigen, and cultured for 0, 4, and 8 days. Then, the growth of CD4+ T cells was identified through flow cytometry.

As a result, it was found that, in the test group using the liposomal EG-IM, the growth efficiency of CD4+ T cells was the most superior to that in the test group using the EG-IM or liposome alone (FIG. 16 in graph B).

3. Cytokine Analysis

Two weeks after the final administration, mice were anesthetized, spleen and lung tissues were extracted and separated into single cells, and the cells were stimulated with 5 μg/ml of an aP antigen and cultured for 24 hours. Then, cells secreting IFN-γ cytokine were analyzed by ELISPOT ELISA (Millipore). The white graph shows the results of spleen cells, and the black graph shows the results of lung cells. In addition, spleen cells were stimulated with 5 μg/ml of an aP antigen and cultured for 72 hours, and the amount of secreted IFN-γ cytokine was analyzed using sandwich ELISA (R&D systems).

Figure 17:
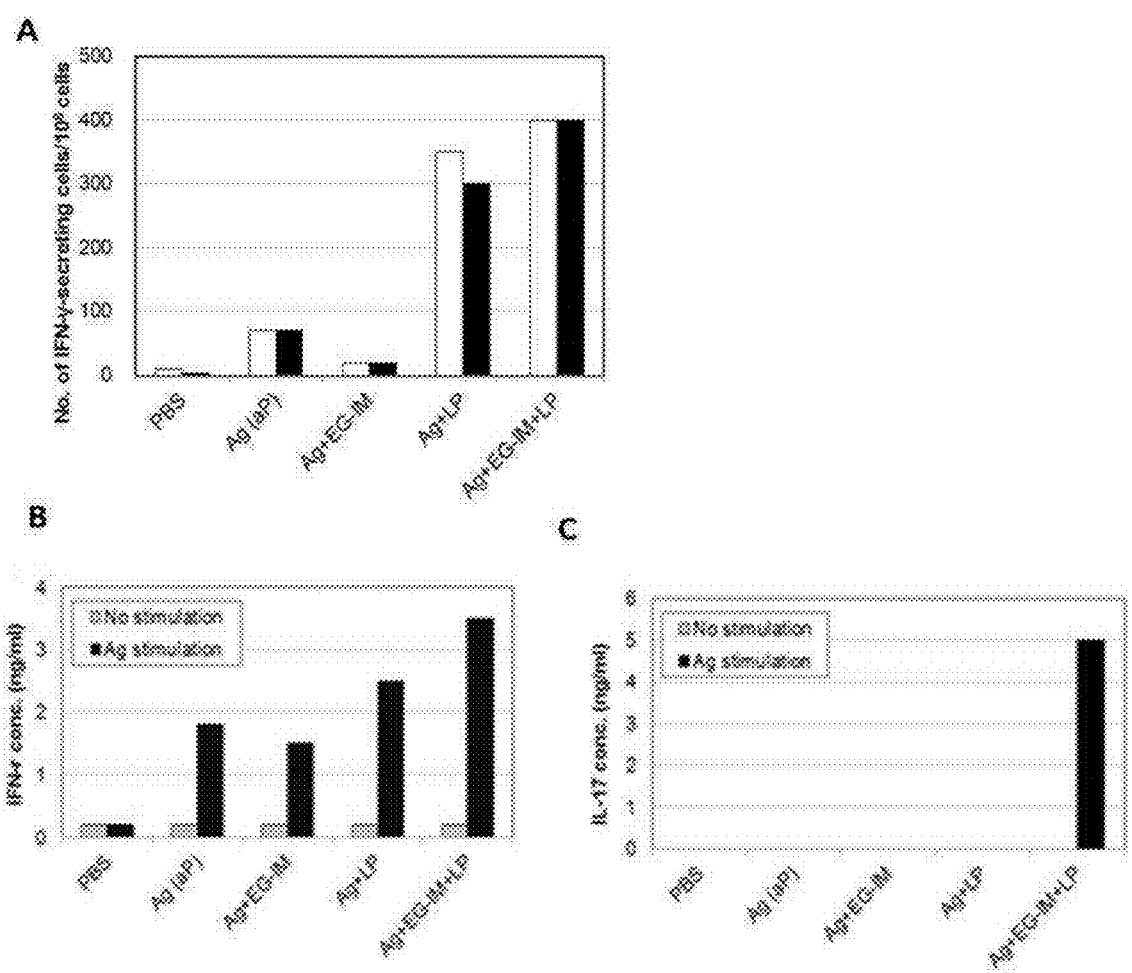
FIG. 17 in graph A shows the amount of IFN-γ cytokine secretion after administration of a pertussis vaccine, wherein a white graph shows the results from spleen cells and a black graph shows the results from lung cells. Graphs B and C show ability to induce IFN-γ and IL-17 upon administration of the pertussis vaccine, respectively.

As a result, the test group using liposomal EG-IM increased the number of cells secreting IFN-γ, as compared to the test group using the EG-IM or liposome alone (FIG. 17 in graph A). In addition, the test group using the liposomal EG-IM had excellent ability to secrete IFN-γ and IL-17 cytokines (FIG. 17 in graphs B and C). In addition, the pertussis vaccine of the present invention containing the liposomal EG-IM had excellent ability to induce cellular immunity.

Example 8: Analysis of Immunogenicity of Liposomal EG-IM in Varicella-Zoster Virus Vaccine A recombinant varicella-zoster virus (VZV) gE antigen was used in order to identify the immunogenicity enhancement effect of the liposomal EG-IM in a varicella-zoster virus vaccine. An attenuated VZV was subcutaneously administered to 6-week-old C57BL/6 mice (SLC, Japan) to prepare a priming model. After 4 weeks, a varicella-zoster virus (VZV) vaccine prepared by mixing the recombinant VZV gE antigen with alum, an EG-IM and a liposomal EG-IM as immune adjuvants was intramuscularly administered to 6-week-old BALB/c mice (SLC, Japan) twice at intervals of two weeks. Regarding the amounts of administration, the recombinant VZV gE antigen was administered in 5 μg/mouse, the EG-IM was administered in 2 or 3 μg/mouse, and the liposomal EG-IM was administered in 50 μg/mouse. As a control group, Zostavax (Merck, USA), a commercially available vaccine, was diluted to ¹/₁₀ the human dose and administered once to the mice. In addition, the comparison was conducted under the condition that the composition ratio of the liposome, which is an ingredient of the liposomal EG-IM, was changed to DOTAP:DMPC=1:1 or DOTAP:DMPC=1:2.

1. Cytokine Analysis

Four weeks after the final administration, mice were anesthetized, spleen tissues were extracted and separated into single cells, and the cells were stimulated with 1,000 PFU/mL of Zostavax (attenuated virus) or 4 μg/ml of a gE peptide mix and cultured for 72 hours. Then, the amount of IFN-γ cytokine secretion in the cell culture was analyzed using an ELISA kit (R&D systems). In addition, spleen cells were stimulated with 1,000 PFU/mL of Zostavax (attenuated virus) or 4 μg/ml of a gE peptide mix. After 24 hours, the cells secreting IFN-γ cytokine were analyzed by ELISPOT ELISA (Millipore).

Figure 18:
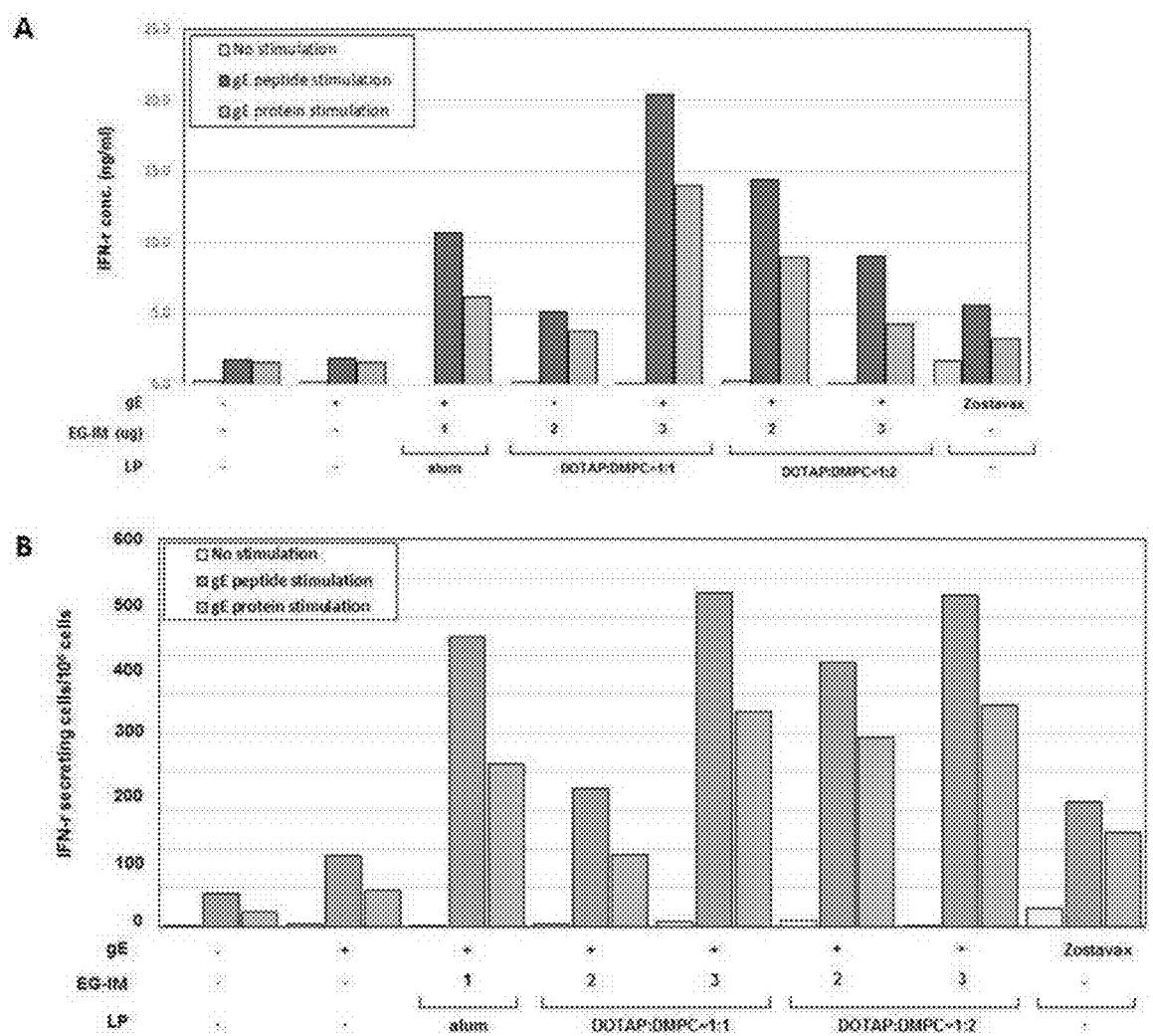
FIG. 18 shows the amount of IFN-γ cytokine secretion after administration of a varicella-zoster virus vaccine containing liposomal EG-IM.

As a result, the test group using the liposomal EG-IM increased secretion of IFN-γ as compared to the test group using the EG-IM alone, and increased secretion of IFN-γ as compared to Zostavax (Merck, USA), a commercially available vaccine (FIG. 18). Therefore, the varicella-zoster virus vaccine of the present invention containing the liposomal EG-IM had excellent ability to induce cellular immunity.

2. Analysis of Synergistic Effect Through Addition of Lipid Composition

Cholesterol (chol), squalene and tricaprin were further mixed as lipid ingredients added to the composition of the liposomal EG-IM in order to identify whether or not a synergistic effect occurred. Each of the vaccines was intramuscularly injected twice at intervals of 2 weeks, mice were anesthetized 2 weeks or 4 weeks after the final administration, and the spleen tissues were extracted, stimulated with 10 μg/ml of a recombinant VZV gE, and cultured for 72 hours. Then, the amount of IFN-γ cytokine secreted in the cell culture was analyzed by ELISA kit (R&D systems). In addition, spleen cells were stimulated with 4 μg/ml of a gE peptide mix and cultured for 24 hours. Then, IFN-γ cytokine-secreting cells were analyzed using an ELISPOT kit (Millipore).

As a result, IFN-γ secretion was enhanced in a liposomal EG-IM, which further contained cholesterol (FIG. 19), squalene (FIG. 20) and tricaprin (FIG. 21). Therefore, it was found that the vaccine further containing cholesterol, squalene and tricaprin as additional lipid ingredients in addition to the liposomal EG-IM had superior ability to induce cellular immunity, as compared to the case where the liposomal EG-IM was used alone.

3. Analysis of Synergistic Effect Through Addition of Immune Adjuvant

Whether or not a synergistic effect occurred when further adding Quil A, a saponin-based substance, as an additional adjuvant to a liposomal EG-IM was observed. Each vaccine was intramuscularly injected twice at intervals of 2 weeks. 4 weeks after the last administration, mice were anesthetized and spleen tissues were collected and separated into single cells. The cells were stimulated with 4 µg/ml of a recombinant VZV gE peptide mix or 1,000 PFU/mL of Zostavax and cultured for 24 hours. Then, cells secreting IFN-γ cytokine were analyzed using an ELISPOT kit (Millipore).

As a result, IFN-γ secretion was enhanced in a liposomal EG-IM, which further contained the saponin-derived substance Quil A (FIG. 22). Thus, it was found that the vaccine further containing the saponin-derived substance as an additional immune enhancer in addition to the liposomal EG-IM had superior ability to induce cellular immunity, as compared to the case where EG-IM was used alone.

4. Analysis of Synergistic Effect Depending on Formulation

In order to determine the difference in immunogenicity depending on the final formulation of the varicella-zoster virus (VZV) vaccine, the experiment was conducted on a simple mixed vaccine (+) and a mixed and lyophilized vaccine (/). Each vaccine composition was intramuscularly administered to seven-week-old BALB/c mice (SLC, Japan) twice at intervals of two weeks. 2 weeks after the last administration, the mice were anesthetized and spleen tissues were extracted and separated into single cells. The cells were stimulated with 5 µg/ml of a recombinant VZV gE antigen and cultured for 72 hours. Then, the levels of IL-5 and IFN-γ cytokines secreted in the cell culture solution were analyzed by sandwich ELISA (R&D systems, DY485; DY405).

Figure 23:
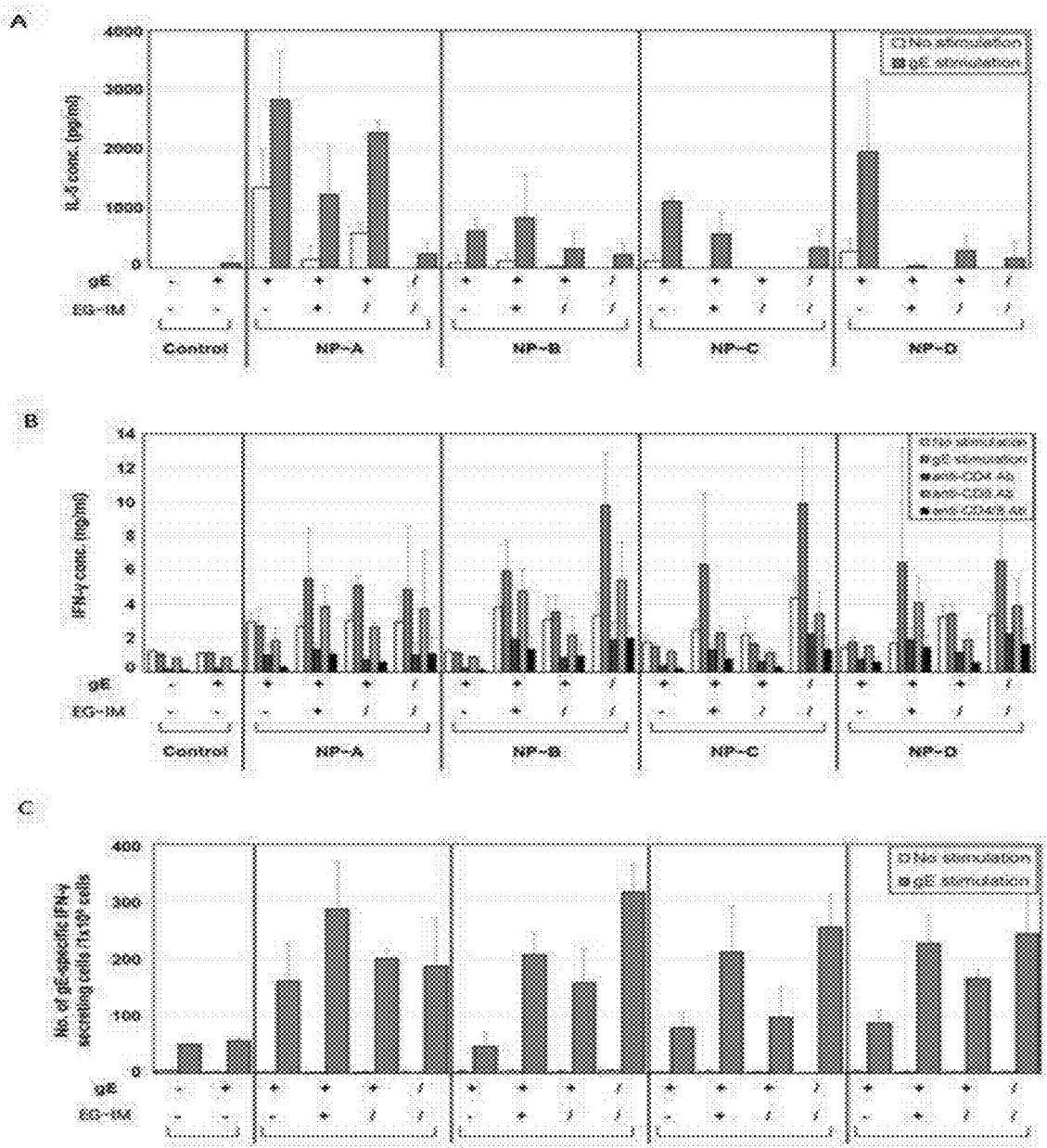
FIG. 23 shows an immunogenicity analysis depending on final formulation of a varicella-zoster virus vaccine containing liposomal EG-IM. Graph A shows the amount of secreted IL-5 cytokine, and graphs B and C show the amount of secreted IFN-γ cytokine, wherein NP-A represents DDA/DOPC, NP-B represents DOTAP/DMPC, NP-C represents DOTAP/DMPC/squalene, NP-D represents DOTAP/DMPC/tricaprin, + represents a simple mixed formulation, and/represents a mixed and lyophilized formulation.

In FIG. 23, NP-A represents DOTAP/DOPC, NP-B represents DOTAP/DMPC, NP-C represents DOTAP/DMPC/squalene, NP-D represents DOTAP/DMPC/tricaprin, + represents a simple mixed formulation, and/represents a mixed and lyophilized formulation.

As a result, the formulation obtained by lyophilizing the liposomal EG-IM with the antigen enhanced IFN-γ secretion the most, but hardly enhanced IL-5 secretion (FIG. 23). Thus, it was found that the formulation obtained by lyophilizing the liposomal EG-IM and the antigen had excellent ability to induce Th1-type cellular immunity.

INDUSTRIAL APPLICABILITY

The present invention overcomes the physicochemical instability of liposomes and is thus advantageous in terms of production, delivery and storage, and has benefits as an immune delivery system owing to improved stability. In addition, the present invention contains all of an antigen, an immune modulator and a cationic liposome, thereby exerting improved immunity enhancement efficacy as compared to a case where an immune modulator is used alone.

The invention claimed is:

1. A composition for enhancing immunity comprising:
   (a) an immune modulator represented by the following Formula 1:

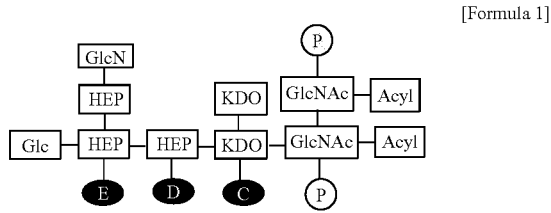

[Formula 1]

wherein Glc is glucose, GlcN is glucosamine, HEP is heptose, KDO is 2-keto-3-deoxy-octonate, GlcNAc is N-acetylglucosamine, P is phosphate, and C to E are positions to which phosphate can be bonded, wherein each phosphate is bonded at a position selected from the group consisting of C, E, CD, CE, DE, and CDE of Formula 1; and
   (b) a cationic liposome.

2. The composition according to claim 1, wherein the cationic liposome is a cationic lipid selected from the group consisting of dimethyldioctadecylammonium bromide (DDA), 1,2-dioleoyl-3-trimethylammonium propane (DOTAP), 3β-[N-(N',N'-dimethylaminoethane) carbamoyl] cholesterol (DC-Chol), 1,2-dioleoyloxy-3-dimethylammonium propane (DODAP), 1,2-di-O-octadecenyl-3-trimethylammonium propane (DOTMA), 1,2-dimyristoleoyl-sn-glycero-3-ethylphosphocholine (14:1 Ethyl PC), 1-palmitoyl-2-oleoyl-sn-glycero-3-ethylphosphocholine (16:0-18:1 Ethyl PC), 1,2-dioleoyl-sn-glycero-3-ethylphosphocholine (18:1 Ethyl PC), 1,2-distearoyl-sn-glycero-3-ethylphosphocholin (18:0 Ethyl PC), 1,2-dipalmitoyl-sn-glycero-3-ethylphosphocholine (16:0 Ethyl PC), 1,2-dimyristoyl-sn-glycero-3-ethylphosphocholine (14:0 Ethyl PC), 1,2-dilauroyl-sn-glycero-3-ethylphosphocholin (12:0 Ethyl PC), N1-[2-((1S)-1-[(3-aminopropyl)amino]-4- [di(3-amino-propyl)amino]butylcarboxamido)ethyl]3,4-di[oleyloxy]-benzamide (MVL5), 1,2-dimyristoyl-3-dimethylammonium-propane (14:0 DAP), 1,2-dipalmitoyl-3-dimethylammonium-propane (16:0 DAP), 1,2-distearoyl-3-dimethylammonium-propane (18:0 DAP), N-(4-carboxybenzyl)-N,N-dimethyl-2,3-bis(oleoyloxy)propan-1-aminium (DOBAQ), 1,2-stearoyl-3-trimethylammonium-propane (18:0 TAP), 1,2-dipalmitoyl-3-trimethylammonium-propane (16:0 TA), 1,2-dimyristoyl-3-trimethylammonium-propane (14:0 TAP) and N4-cholesteryl-spermine (GL67).

3. The composition according to claim 2, wherein the cationic liposome further comprises a neutral lipid selected from the group consisting of 1,2-dimyristoyl-sn-glycero-3-phosphorylcholine (DMPC), 1,2-dioleoyl-sn-glycero-3-phosphocholine (DOPC), 1,2-dioleoyl-sn-glycero-3-phosphoethanolamine (DOPE), 1,2-dipalmitoyl-sn-glycero-3-phosphocholine (DPPC), 1,2-distearoyl-sn-glycero-3-phosphocholine (DSPC), 1,2-dilinoleoyl-sn-glycero-3-phosphocholine (DLPC), phosphoethanol amine (PE), and phosphatidyl choline (PC).

4. A vaccine composition comprising:
   (a) an antigen; and
   (b) the composition for enhancing immunity according to claim 1 as an active ingredient.

5. The vaccine composition according to claim 4, wherein the antigen is selected from the group consisting of a peptide, a protein, a nucleic acid, a sugar, a pathogen, an attenuated pathogen, an inactivated pathogen, a virus, a virus-like particle (VLP), a cell or a cell fragment.

6. The vaccine composition according to claim 4, wherein the antigen is selected from the group consisting of an antigen of Zika virus, an antigen of Japanese encephalitis virus, an antigen of *Mycobacterium tuberculosis*, an antigen of pertussis, an antigen of varicella-zoster virus, an antigen of *Haemophilus influenzae* type B (HIB), an antigen of Middle East Respiratory Syndrome (MERS) virus, an antigen of *Pseudomonas aeruginosa*, an antigen of anthrax, an antigen of hepatitis A virus (HAV), an antigen of hepatitis B virus (HBV), an antigen of hepatitis C virus (HCV), an antigen of human immunodeficiency virus (HIV), an antigen of herpes simplex virus (HSV), an antigen of *Neisseria meningitidis*, an antigen of *Corynebacterium diphtheria*, an antigen of *Bordetella pertussis*, an antigen of *Clostridium tetani*, an antigen of human papilloma virus (HPV), an antigen of Enterococci, an antigen of *Staphylococcus aureus*, an antigen of *Klebsiella pneumoniae*, an antigen of *Acinetobacter baumannii*, an antigen of *Enterobacter*, an antigen of *Helicobacter pylori*, an antigen of malaria, an antigen of a dengue virus, an antigen of *Orientia tsutsugamushi*, an antigen of severe fever with thrombocytopenia syndrome Bunyavirus (SFTS Bunyavirus), an antigen of severe acute respiratoty syndrome-coronavirus (SARS-CoV), an antigen of an influenza virus, an antigen of an Ebola virus and an antigen of *Diplococcus pneumoniae*.

7. The vaccine composition according to claim 4, wherein the vaccine is an inactivated vaccine, an attenuated vaccine, a subunit vaccine, a conjugate vaccine, a recombinant vaccine, a monovalent vaccine, a multivalent vaccine, or a mixed vaccine.

8. The vaccine composition according to claim 4, wherein the vaccine is selected from the group consisting of a Zika vaccine, a Japanese encephalitis vaccine, a tuberculosis vaccine, a pertussis vaccine, a varicella-zoster virus (VZV) vaccine, a varicella vaccine, a *Haemophilus influenzae* type B vaccine, a MERS vaccine, a *Pseudomonas aeruginosa* vaccine, a cancer vaccine, an anthrax vaccine, a HAV vaccine, an HBV vaccine, an HCV vaccine, an HIV vaccine, a meningococcal vaccine, a diphtheria vaccine, a tetanus vaccine, a multidrug-resistant bacteria vaccine, an Enterococci vaccine, a *Staphylococcus aureus* vaccine, a *Klebsiella pneumoniae* vaccine, an *Acinetobacter baumannii* vaccine, an *Enterobacter* vaccine, a *Helicobacter pylori* vaccine, a malaria vaccine, a dengue virus vaccine, an *Orientia tsutsugamushi* vaccine, a severe fever with thrombocytopenia syndrome Bunyavirus (SFTS bunyavirus) vaccine, a severe acute respiratory syndrome-coronavirus (SARS-CoV) vaccine, an Ebola virus vaccine, an influenza virus vaccine and a *Diplococcus pneumoniae* vaccine.

9. The vaccine composition according to claim 4, wherein the vaccine is a lyophilized formulation.

10. The vaccine composition according to claim 8, wherein the varicella-zoster virus (VZV) vaccine is in a ready-to-use form.

11. The vaccine composition according to claim 4, wherein the vaccine further comprises cholesterol, squalene or tricaprin.

12. The vaccine composition according to claim 4, wherein the vaccine further comprises saponin, Quil A or QS21 as a saponin-derived substance.

13. A method for preparing the composition for enhancing immunity according to claim 1 comprising:
(a) preparing a solution containing an immune modulator represented by the following Formula 1:

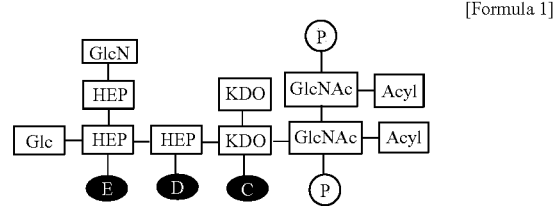

[Formula 1]

wherein Glc is glucose, GlcN is glucosamine, HEP is heptose, KDO is 2-keto-3-deoxy-octonate, GlcNAc is N-acetylglucosamine, P is phosphate, and C to E are positions to which phosphate can be bonded, wherein each phosphate is bonded at a position selected from the group consisting of C, E, CD, CE, DE, and CDE of Formula 1;
(b) dissolving a lipid in an organic solvent to prepare a lipid mixed solution;
(c) lyophilizing the lipid mixed solution of step (b) to remove the organic solvent; and
(d) rehydrating the substance obtained in step (c), and then mixing the substance with the solution of step (a), thereby forming a composition for enhancing immunity.

14. A method for preparing the vaccine composition according to claim 4 comprising:
(a) preparing a solution containing an immune modulator represented by the following Formula 1:

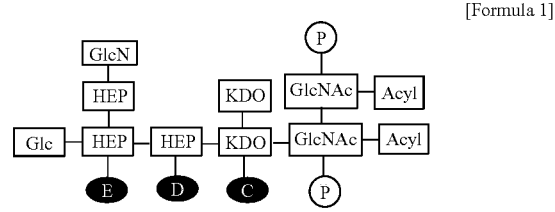

[Formula 1]

wherein Glc is glucose, GlcN is glucosamine, HEP is heptose, KDO is 2-keto-3-deoxy-octonate, GlcNAc is N-acetylglucosamine, P is phosphate, and C to E are positions to which phosphate can be bonded, wherein each phosphate is bonded at a position selected from the group consisting of C, E, CD, CE, DE, and CDE of Formula 1;
(b) dissolving a lipid in an organic solvent to prepare a lipid mixed solution;
(c) lyophilizing the lipid mixed solution of step (b) to remove the organic solvent;
(d) rehydrating the substance obtained in step (c), thereby forming a liposome; and
(e) adding the solution of step (a) and an antigen to the liposome of step (d), followed by lyophilizing again.

* * * * *

UNITED STATES PATENT AND TRADEMARK OFFICE
CERTIFICATE OF CORRECTION

PATENT NO. : 10,874,733 B2
APPLICATION NO. : 16/346401
DATED : December 29, 2020
INVENTOR(S) : Yang Je Cho et al.

It is certified that error appears in the above-identified patent and that said Letters Patent is hereby corrected as shown below:

In the Specification

Column 2, Lines 27-28, "J Biol Chem. December 17; 274(50:36579-84, 1999)" should be -- J Biol Chem. December 17; 274 (51):36579- 84, 1999) --.

Column 4, Lines 12-18, The following passage appearing at Column 4, Lines 12-15, "The patent or application file contains at least one drawing executed in color. Copies of this patent or patent application publication with color drawing(s) will be provided by the Office upon request and payment of the necessary fee." should be moved to follow the heading "BRIEF DESCRIPTION OF THE DRAWINGS" at Column 4, Line 17, so that such passage appears before the paragraph beginning at Column 4, Line 19, with the words "FIG. 1 in image A ..." and ending at Column 4, Line 26, with "... (EG-IM).".

Signed and Sealed this
Twenty-third Day of February, 2021

Drew Hirshfeld
*Performing the Functions and Duties of the
Under Secretary of Commerce for Intellectual Property and
Director of the United States Patent and Trademark Office*